(12) United States Patent
Koya et al.

(10) Patent No.: US 7,385,084 B2
(45) Date of Patent: Jun. 10, 2008

(54) BIS(THIO-HYDRAZIDE AMIDE) SALTS FOR TREATMENT OF CANCERS

(75) Inventors: Keizo Koya, Chestnut Hill, MA (US); Lijun Sun, Harvard, MA (US); Elena Kostik, Arlington, MA (US); Farid Vaghefi, Watertown, MA (US); Shoujun Chen, Bedford, MA (US); Noriaki Tatsuta, Lexington, MA (US); Guiqing Liang, Concord, MA (US); Takayo Inoue, Malden, MA (US); Zhi-Qiang Xia, Acton, MA (US)

(73) Assignee: Synta Pharmaceutical Corp., Lexington, MA (US)

(*) Notice: Subject to any disclaimer, the term of this patent is extended or adjusted under 35 U.S.C. 154(b) by 0 days.

(21) Appl. No.: 11/157,213

(22) Filed: Jun. 20, 2005
(Under 37 CFR 1.47)

(65) Prior Publication Data

US 2006/0135595 A1   Jun. 22, 2006

Related U.S. Application Data

(60) Provisional application No. 60/681,368, filed on May 16, 2005, provisional application No. 60/582,596, filed on Jun. 23, 2004.

(51) Int. Cl.
   *C07C 327/38* (2006.01)
   *A61K 31/16* (2006.01)
(52) U.S. Cl. ............... 564/74; 514/422; 514/599; 548/518
(58) Field of Classification Search ........... 514/422, 514/599; 564/74; 548/518
   See application file for complete search history.

(56) References Cited

U.S. PATENT DOCUMENTS

| | | | |
|---|---|---|---|
| 4,012,360 | A | 3/1977 | Schwarzenbach et al. |
| 6,013,836 | A | 1/2000 | Hsu et al. |
| 6,172,108 | B1 | 1/2001 | Vega et al. |
| 6,172,188 | B1 | 1/2001 | Thastrup et al. |
| 6,235,787 | B1 | 5/2001 | Broadhurst et al. |
| 6,365,745 | B1 | 4/2002 | Matsui et al. |
| 6,399,659 | B2 | 6/2002 | Usui et al. |
| 6,435,787 | B1 | 8/2002 | John |
| 6,455,515 | B2 | 9/2002 | Gypser et al. |
| 6,656,971 | B2 | 12/2003 | Wu et al. |
| 6,703,426 | B1 | 3/2004 | Miles et al. |
| 6,762,204 | B2 * | 7/2004 | Koya et al. .......... 514/599 |
| 6,800,660 | B2 | 10/2004 | Koya et al. |
| 6,825,235 | B2 | 11/2004 | Chen et al. |
| 6,924,312 | B2 | 8/2005 | Koya et al. |
| 7,001,923 | B2 | 2/2006 | Koya et al. |
| 7,037,940 | B2 | 5/2006 | Koya et al. |
| 7,074,952 | B2 | 7/2006 | Chen et al. |
| 2003/0045518 | A1 | 3/2003 | Koya et al. |
| 2003/0119914 | A1 | 6/2003 | Koya et al. |
| 2004/0225016 | A1 | 11/2004 | Koya et al. |
| 2006/0116374 | A1 | 6/2006 | Koya et al. |
| 2006/0122183 | A1 | 6/2006 | Koya et al. |
| 2006/0142386 | A1 | 6/2006 | Barsoum |
| 2006/0142393 | A1 | 6/2006 | Sherman et al. |
| 2006/0270873 | A1 | 11/2006 | Chen et al. |
| 2006/0281811 | A1 | 12/2006 | Chen et al. |
| 2007/0088057 | A1 | 4/2007 | Lunsmann et al. |

FOREIGN PATENT DOCUMENTS

| | | |
|---|---|---|
| DE | 2037257 | 2/1972 |
| FR | 2097737 | 4/1972 |
| JP | 50-91056 | 7/1975 |
| WO | WO 94/10995 | 5/1994 |
| WO | WO 99/34796 | 7/1999 |
| WO | WO 03/006428 A | 1/2003 |
| WO | WO 03/006430 A | 1/2003 |
| WO | WO 06/113572 | 10/2006 |
| WO | WO 06/113695 | 10/2006 |

OTHER PUBLICATIONS

Golub et al, Science, vol. 286, 1999, pp. 531-537.*
H. Bräniger, "Hydrazide und Hydrazidderivate von Dicarbonsäuren," Pharmaceutical-Chemical Institute of University of Rostock, Supplied by the "British Library" 25(5-6) 279-283 (1970).

(Continued)

*Primary Examiner*—Shailendra Kumar
(74) *Attorney, Agent, or Firm*—Hamilton, Brook, Smith & Reynolds, P.C.

(57) ABSTRACT

Disclosed are bis(thio-hydrazide amide) disalts, which are represented by Structural Formula (I):

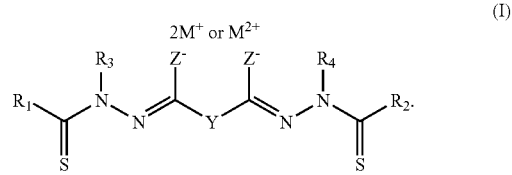

Y is a covalent bond or a substituted or unsubstituted straight chained hydrocarbyl group. $R_1$-$R_4$ are independently —H, an aliphatic group, a substituted aliphatic group, an aryl group or a substituted aryl group, or $R_1$ and $R_3$ taken together with the carbon and nitrogen atoms to which they are bonded, and/or $R_2$ and $R_4$ taken together with the carbon and nitrogen atoms to which they are bonded, form a non-aromatic heterocyclic ring optionally fused to an aromatic ring. Z is —O or —S. $M^+$ is a pharmaceutically acceptable monovalent cation and $M^{2+}$ is a pharmaceutically acceptable divalent cation.

Also, disclosed are pharmaceutical compositions comprising a bis(thio-hydrazide amide) disalt described above. Further disclosed are methods of treating a subject with cancer. The methods comprise the step of administering an effective amount of a bis(thio-hydrazide amide) disalt described above.

34 Claims, 24 Drawing Sheets

OTHER PUBLICATIONS

Al-Talib, M. et al., "Diacyl Acid Dihydraides," *Magnetic Resonance in Chemistry* 28:1072-1078 (1990).

Chuiguk, V,A., and Nemazanyi, A.G., "Mesoionic Methine Dyes of Biquaternary Salts of Diheteroaryl Methanes - Derivatives of 1, 3, 4 - oxa (thia) Diazoles and 1, 2, 4 - Triazoles," Kiev. Gos. Univ., Kiev, USSR, Ukrainskii Khimicheskii Zhurnal, Russian Edition, 50(5):519-524 (1984). Abstract, Accession No. 1984:630420, HCAPLUS Database.

Barrett, William G. and McKay, Donald, "Decomposition and Cycloaddition Reactions of Some Bis(azodicarbonyl) Compounds," Journal of Chem. Soc. (4):1046-1052 (1975).

Mitsui Toatsu Chem. Inc., Abstract of Japanese Patent No. 308024, published Dec. 25, 1986. from Derwent Publications Ltd.

Honshu Paper Mfg. Co. Ltd, Abstract of JApanese Patent No. 182050, published Feb. 13, 1996.

Molina, P., et al., XP-01118868 "Methyl 2-Methyldithiocarbazate in Heterocyclic Synthesis: Preparation of 2,5-Disubstituted 1,3,4-Thiadiazoles, Bis(1,3,4-Thiadiazolium) Salts and Macrocycles containing 1,3,4-Thiadiazole Subunits, X-Ray Crystal Structure of 2,2'-Bis[4,5-dihydro-5-(2-hydroxyethylimino)-4-methyl-1,3,4-thiadiazole], " *J. Chem. Soc. Perkin Trans. 1 s* 5:1159-1166 (1991).

Molina, P., et al., XP-001118802 "Preparation of a Novel Type of Ligands Incorporating Two or Three 1,3,4-Thiadiazole Units," *Heterocycles* 36(6):1263-1278 (1993).

Chuyguk, V.A. and Nemazanyj A.G., "Mesoionic Methine Dyes from Biquarternary Salts of Dihetarylmethanes - 1,3,4-Oxa(thia)diazoles and 1,2,4-Thiazoles Derivatives," *Ukr, Khim. Zhurn.* 48:520 (1984). "Remarks" paper as submitted by applicant's attorney.

Staleri, M.A., et al., "Site-specific conjugation and labelling of prostate antibody 7E11C5.3 (CYT-351) with technetium-99m" *European Journal of Nuclear Medicine* 24(6):651-654, (1997).

Twomey, D., "Anticancer Agents-IX. Derivatives of Pyridine, Pyridazine and Phthalazine," *Proceedings of the Royal Irish Academy, vol. 74*, Sect. B:37-52, (1974).

Schwarz et al., CA77:48081, 1972.

Rupp, Walter, CA76:126992, 1972.

Barry, V.C., et al., "Anticancer Agents-III. Synthesis and Anticancer Activity of Some Bis-Thiosemicarbazones and Thoiosemicarbazides," *Proc. R.I.A.* Sect. B*(65)*:309-324 (1967).

O'Callaghan, C.N., "Anticancer Agents-X Cyclisation of 1-Acyl-4-Alkylthiosemicarbazide Derivatives to 1,2,4-Triazoline-3-Thiones in the Presence of Hydrazine," *Proc. R.I.A.*, Sect. B*(74)*:455-461 (1974).

Merlin, J.L., et al., In Vitro Comparative Evaluation of Trastuzumab (Herceptin®) Combined with Paciltaxel (Taxol®) or Docetaxel (Taxotere®) in HER2-Expreesing Human Breat Cancer Cell Lines, *Annals of Oncology 13*: 1743-1748 (2002).

Asahi Chemical Ind. KK. Abstract of Japanese Patent No. 50-91056, Accession No.: 47521Y/27 (1975).

* cited by examiner

BIS(THIO-HYDRAZIDE AMIDE) SALTS FOR TREATMENT OF CANCERS

RELATED APPLICATIONS

This application claims the benefit of U.S. Provisional Patent Application Ser. No. 60/582,596, filed Jun. 23, 2004 and U.S. Provisional Patent Application Ser. No. 60/681,368, filed May 16, 2005. The entire teachings of the above applications are incorporated herein by reference.

BACKGROUND OF THE INVENTION

Many drugs are now available to be used in the treatment of cancer. However, in many cases the cancer fails to respond to the anti-cancer therapy or its growth and/or metastasis is only slowed. Even when a tumor initially responds to an anti-cancer therapy by decreasing in size or going into remission, the tumor often develops resistance to the drug. For these reasons, there has been a need for new anti-cancer agents and for new drugs which can be used to treat multi-drug resistance cancers.

Certain bis(thio-hydrazide amide) compounds have been described by the present inventors as being significantly cytotoxic to cancer cells, including cancer cells that have become multi-drug resistant, and for enhancing the anti-cancer activity of other anti-cancer agents, such as paclitaxel and Epothilone D (see, e.g., U.S. Publication Nos. 2004/0225016 A1, 2003/0045518 and 2003/0119914, the entire contents of which are incorporated herein by reference).

SUMMARY OF THE INVENTION

It has now been found that bis(thio-hydrazide amide) disalts show unexpectedly high water solubility and bioavailability. For example, disodium and dipotassium salts of Compounds (1) and (2), show water solubility of greater than 1,000 mg/ml, compared with a solubility of about 0.1 mg/ml for the corresponding neutral form of Compounds (1) and (2) (see Examples 2, 10 and 15). Similar increases in solubility were observed for the disodium and dipotassium salts of Compounds (12), (13) and (14) (see Examples 12-15). Moreover, the bioavailability of the disodium salt of Compound (1) was 80%, whereas the bioavailability of the neutral compound was 4.8% (see Example 16). A representative tautomeric structure of Compounds (1) and (2) are shown below:

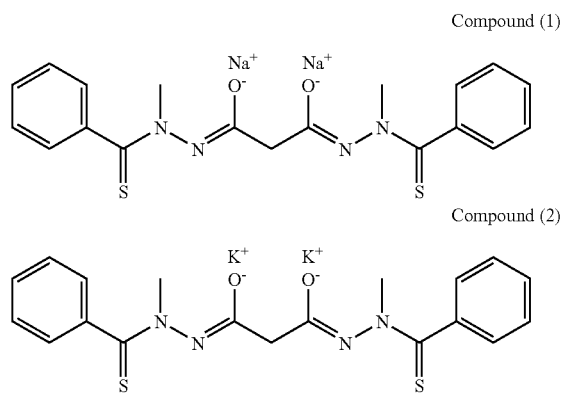

Based on these results, novel bis(thio-hydrazide amide) disalts, pharmaceutical compositions comprising a bis(thio-hydrazide amide) disalt and methods of treatment using a bis(thio-hydrazide amide) disalt are disclosed.

One embodiment of the present invention is a compound represented by the following Structural Formula (I), and its tautomeric forms:

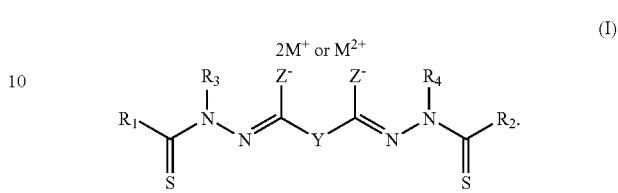

Y is a covalent bond or a substituted or unsubstituted straight chained hydrocarbyl group. $R_1$-$R_4$ are independently —H, an aliphatic group, a substituted aliphatic group, an aryl group or a substituted aryl group, or $R_1$ and $R_3$ taken together with the carbon and nitrogen atoms to which they are bonded, and/or $R_2$ and $R_4$ taken together with the carbon and nitrogen atoms to which they are bonded, form a non-aromatic heterocyclic ring optionally fused to an aromatic ring. Z is —O or —S. $M^+$ is a pharmaceutically acceptable monovalent cation and $M^{2+}$ is a pharmaceutically acceptable divalent cation.

Another embodiment of the present invention is a pharmaceutical composition comprising a bis(thio-hydrazide amide) disalt disclosed herein and a pharmaceutically acceptable carrier or diluent. The pharmaceutical compositions can be used in therapy, for example, as anti-cancer agents.

The present invention also provides for a method of treating a subject with a cancer. The method comprises administering to the subject an effective amount of a bis(thio-hydrazide amide) disalt disclosed herein. The bis(thio-hydrazide amide) disalt is administered as a mono-therapy (i.e., as the only anti-cancer drug administered to the subject) or is co-administered with one or more other anti-cancer drugs.

The use of the bis(thio-hydrazide amide) disalts disclosed herein in the manufacture of a medicament for the purpose of treating cancer in an individual is also provided in the present invention.

The present invention also provides for a method of preparing a bis(thio-hydrazide amide) disalt. The method includes the steps of combining a neutral bis(thio-hydrazide amide), an organic solvent and a base to form a bis(thio-hydrazide amide) solution; and combining the solution and an organic antisolvent, thereby precipitating a disalt of the bis (thio-hydrazide amide).

In various embodiments, a method of preparing a bis(thio-hydrazide amide) disalt includes the steps of combining a neutral bis(thio-hydrazide amide) and an organic solvent selected from methanol, ethanol, acetone, and methyl ethyl ketone to make a mixture; adding at least two equivalents of a base selected from sodium hydroxide, potassium hydroxide, sodium methoxide, potassium methoxide, sodium ethoxide and potassium ethoxide to the mixture, thereby forming a solution; and combining the solution and an organic antisolvent selected from pentane, hexane, cyclohexane, heptane, petroleum ether, ethyl acetate, and diethyl ether to precipitate the disalt of the bis(thio-hydrazide amide).

In various embodiments, a method of preparing a bis(thio-hydrazide amide) disalt, includes the steps of combining a neutral bis(thio-hydrazide amide), an organic solvent and a base to form a bis(thio-hydrazide amide) solution; and separating a disalt of the bis(thio-hydrazide amide).

In various embodiments, a method of preparing a bis(thio-hydrazide amide) disalt includes the steps of combining a neutral bis(thio-hydrazide amide), an organic solvent and a base to form a bis(thio-hydrazide amide) solution; and combining the solution and methyl tert-butyl ether, thereby precipitating a disalt of the bis(thio-hydrazide amide).

In various embodiments, a method of preparing a bis(thio-hydrazide amide) disalt includes the steps of combining a neutral bis(thio-hydrazide amide) and an organic solvent selected from methanol, ethanol, acetone, and methyl ethyl ketone to make a mixture; adding at least two equivalents of a base selected from sodium hydroxide, potassium hydroxide, sodium methoxide, potassium methoxide, sodium ethoxide and potassium ethoxide to the mixture, thereby forming a solution; and combining the solution and methyl tert-butyl ether to precipitate the disalt of the bis(thio-hydrazide amide).

Because the disclosed bis(thio-hydrazide amide) disalts have excellent water solubility and high bioavailability, they can be used in water-based formulations suitable for intravenous and oral administration. In addition, the disclosed bis (thio-hydrazide amide) disalts are relatively non-toxic, which allows the use of the disclosed disalts at relatively high doses with minimal side effects. The high water solubility of the compounds, in turn, makes high dose formulations possible.

The bis(thio-hydrazide amide) disalts disclosed herein can be used to treat cancers, including cancers that have become multi-drug resistant. Thus, the disclosed bis(thio-hydrazide amide) disalts can be used to treat cancers where other drug regimens have either failed or become ineffective. Additionally, the disclosed bis(thio-hydrazide amide) disalts are particularly effective when used in combination with other anti-cancer drugs such as paclitaxel or an analog of paclitaxel.

DETAILED DESCRIPTION OF THE INVENTION

Figure 1:
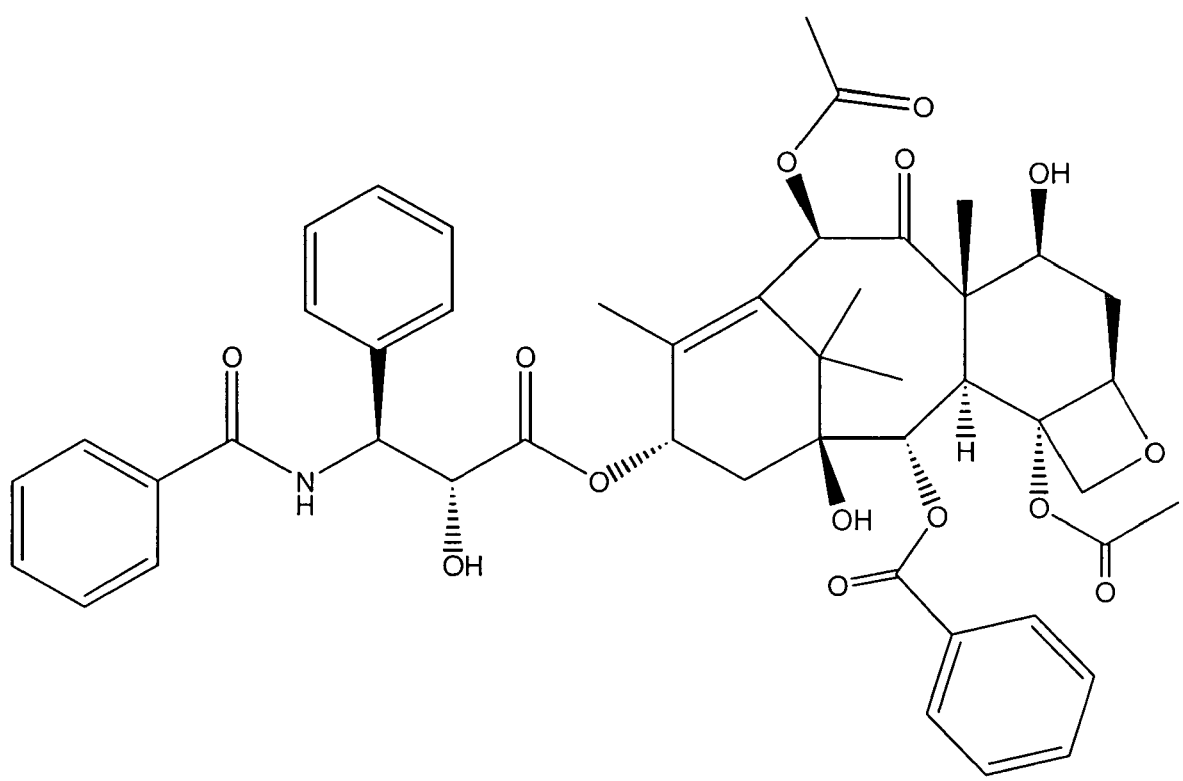
FIG. 1 is the structure of paclitaxel (TAXOL).

The bis(thio-hydrazide amide) disalts of the present invention are represented by Structural Formula (I).

$M^+$ is a pharmaceutically acceptable monovalent cation. $M^{2+}$ is a pharmaceutically acceptable divalent cation. "Pharmaceutically acceptable" means that the cation is suitable for administration to a subject. Examples of $M^+$ or $M^{2+}$ include $Li^+$, $Na^+$, $K^+$, $Mg^{2+}$, $Ca^{2+}$, $Zn^{2+}$, and $NR_4^+$, wherein each R is independently hydrogen, a substituted or unsubstituted aliphatic group (e.g., a hydroxyalkyl group, aminoalkyl group or ammoniumalkyl group) or substituted or unsubstituted aryl group, or two R groups, taken together, form a substituted or unsubstituted non-aromatic heterocyclic ring optionally fused to an aromatic ring. Preferably, the pharmaceutically acceptable cation is $Li^+$, $Na^+$, $K^+$, $NH_3(C_2H_5OH)^+$, $N(CH_3)_3(C_2H_5OH)^+$, arginine or lysine. More preferably, the pharmaceutically acceptable cation is $Na^+$ or $K^+$. $Na^+$ is even more preferred.

In Structural Formula (I), Z is preferably —O. More preferably, Z is —O; $R_1$ and $R_2$ are the same; and $R_3$ and $R_4$ are the same.

In one embodiment, Y in Structural Formula (I) is a covalent bond, —C($R_5R_6$)—, —(CH$_2$CH$_2$)—, trans-(CH=CH)—, cis-(CH=CH)— or —(CC)— group, preferably —C($R_5R_6$)—. $R_1$-$R_4$ are as described above for Structural Formula (I). $R_5$ and $R_6$ are each independently —H, an aliphatic or substituted aliphatic group, or $R_5$ is —H and $R_6$ is a substituted or unsubstituted aryl group, or, $R_5$ and $R_6$, taken together, are a C2-C6 substituted or unsubstituted alkylene group. The pharmaceutically acceptable cation is as described above.

In a preferred embodiment of the present invention, the bis(thio-hydrazide amide) disalt is represented by Structural Formula (II):

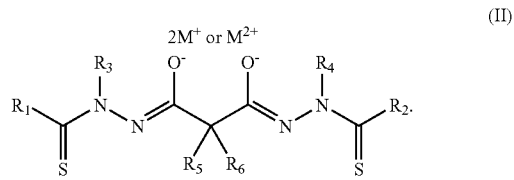

(II)

$R_1$-$R_6$ and the pharmaceutically acceptable cation are as described above for Structural Formula (I).

In one more preferred embodiment of the present invention, the bis(thio-hydrazide amide) disalt is represented by Structural Formula (II) where $R_1$ and $R_2$ are each a substituted or unsubstituted aryl group, preferably a substituted or unsubstituted phenyl group; $R_3$ and $R_4$ are each a substituted or unsubstituted aliphatic group, preferably an alkyl group, more preferably, methyl or ethyl; and $R_5$ and $R_6$ are as described above, but $R_5$ is preferably —H and $R_6$ is preferably —H, an aliphatic or substituted aliphatic group.

Alternatively, $R_1$ and $R_2$ are each a substituted or unsubstituted aryl group; $R_3$ and $R_4$ are each a substituted or unsubstituted aliphatic group; $R_5$ is —H; and $R_6$ is —H, an aliphatic or substituted aliphatic group. Preferably, $R_1$ and $R_2$ are each a substituted or unsubstituted aryl group; $R_3$ and $R_4$ are each an alkyl group; and $R_5$ is —H and $R_6$ is —H or methyl. Even more preferably, $R_1$ and $R_2$ are each a substituted or unsubstituted phenyl group; $R_3$ and $R_4$ are each methyl or ethyl; and $R_5$ is —H and $R_6$ is —H or methyl. Suitable substituents for an aryl group represented by $R_1$ and $R_2$ and an aliphatic group represented by $R_3$, $R_4$ and $R_6$ are as described below for aryl and aliphatic groups.

In a second more preferred embodiment of the present invention, the bis(thio-hydrazide amide) disalt is represented by Structural Formula (II) where $R_1$ and $R_2$ are each a substituted or unsubstituted aliphatic group, preferably a C3-C8 cycloalkyl group optionally substituted with at least one alkyl group, more preferably cyclopropyl or 1-methylcyclopropyl; $R_3$ and $R_4$ are as described above for Structural Formula (I), preferably both a substituted or unsubstituted alkyl group; and $R_5$ and $R_6$ are as described above, but $R_5$ is preferably —H and $R_6$ is preferably —H, an aliphatic or substituted aliphatic group, more preferably —H or methyl.

Alternatively, the bis(thio-hydrazide amide) disalt is represented by Structural Formula (II) where $R_1$ and $R_2$ are each a substituted or unsubstituted aliphatic group; $R_3$ and $R_4$ are as described above for Structural Formula (I), preferably both a substituted or unsubstituted alkyl group; and $R_5$ is —H and $R_6$ is —H or an optionally substituted aliphatic group. Preferably, $R_1$ and $R_2$ are both a C3-C8 cycloalkyl group optionally substituted with at least one alkyl group; $R_3$ and $R_4$ are both as described above for Structural Formula (I), preferably an alkyl group; and $R_5$ is —H and $R_6$ is —H or an aliphatic or substituted aliphatic group. More preferably, $R_1$ and $R_2$ are both a C3-C8 cycloalkyl group optionally substituted with at least one alkyl group; $R_3$ and $R_4$ are both an alkyl group; and $R_5$ is —H and $R_6$ is —H or methyl. Even more preferably, $R_1$ and $R_2$ are both cyclopropyl or 1-methylcyclopropyl; $R_3$ and $R_4$ are both an alkyl group, preferably methyl or ethyl; and $R_5$ is —H and $R_6$ is —H or methyl.

The following are specific examples of bis(thio-hydrazide amide) disalts represented by Structural Formula (II): $R_1$ and $R_2$ are both phenyl; $R_3$ and $R_4$ are both methyl; $R_5$ is —H, and $R_6$ is ethyl; $R_1$ and $R_2$ are both phenyl; $R_3$ and $R_4$ are both phenyl, and $R_5$ and $R_6$ are both methyl; $R_1$ and $R_2$ are both 2-thienyl; $R_3$ and $R_4$ are both phenyl, and $R_5$ and $R_6$ are both methyl; $R_1$ and $R_2$ are both 4-cyanophenyl; $R_3$ and $R_4$ are both methyl; $R_5$ is —H, and $R_6$ is methyl; $R_1$ and $R_2$ are both phenyl; $R_3$ and $R_4$ are both methyl; $R_5$ is —H, and $R_6$ is methyl; $R_1$ and $R_2$ are both phenyl; $R_3$ and $R_4$ are both methyl; $R_5$ is —H, and $R_6$ is benzyl; $R_1$ and $R_2$ are both phenyl; $R_3$ and $R_4$ are both methyl; $R_5$ is —H, and $R_6$ is ethyl; $R_1$ and $R_2$ are both phenyl; $R_3$ and $R_4$ are both ethyl; $R_5$ is —H, and $R_6$ is n-butyl; $R_1$ and $R_2$ are both 2,5-dimethoxyphenyl; $R_3$ and $R_4$ are both methyl; $R_5$ is —H, and $R_6$ is methyl; $R_1$ and $R_2$ are both phenyl; $R_3$ and $R_4$ are both methyl; $R_5$ is —H, and $R_6$ is iso-propyl; $R_1$ and $R_2$ are both 3-nitrophenyl; $R_3$ and $R_4$ are both methyl; $R_5$ is —H, and $R_6$ is methyl; $R_1$ and $R_2$ are both 4-chlorophenyl; $R_3$ and $R_4$ are both methyl; $R_5$ is —H, and $R_6$ is methyl; $R_1$ and $R_2$ are both phenyl; $R_3$ and $R_4$ are both methyl; $R_5$ is —H, and $R_6$ is 3-thienyl; $R_1$ and $R_2$ are both phenyl; $R_3$ and $R_4$ are both methyl, and $R_5$ and $R_6$, taken together, are propylene; $R_1$ and $R_2$ are both 2,3-dimethoxyphenyl; $R_3$ and $R_4$ are both methyl; $R_5$ is —H, and $R_6$ is methyl; $R_1$ and $R_2$ are both 2-chloro-5-methoxy phenyl; $R_3$ and $R_4$ are both methyl; $R_5$ is —H, and $R_6$ is methyl; $R_1$ and $R_2$ are both 2,5-difluorophenyl; $R_3$ and $R_4$ are both methyl; $R_5$ is —H, and $R_6$ is methyl; $R_1$ and $R_2$ are both 2,5-dichlorophenyl; $R_3$ and $R_4$ are both methyl; $R_5$ is —H, and $R_6$ is methyl; $R_1$ and $R_2$ are both 2,6-dimethoxyphenyl; $R_3$ and $R_4$ are both methyl; $R_5$ is —H, and $R_6$ is methyl; $R_1$ and $R_2$ are both 2,5-dimethylphenyl; $R_3$ and $R_4$ are both methyl; $R_5$ is —H, and $R_6$ is methyl; $R_1$ and $R_2$ are both 2,5-dimethoxyphenyl; $R_3$ and $R_4$ are both ethyl; $R_5$ is —H, and $R_6$ is methyl, and $R_1$ and $R_2$ are both 2,5-diethoxyphenyl; $R_3$ and $R_4$ are both methyl; $R_5$ is —H, and $R_6$ is methyl; $R_1$ and $R_2$ are both cyclopropyl; $R_3$ and $R_4$ are both methyl; $R_5$ and $R_6$ are both —H; $R_1$ and $R_2$ are both cyclopropyl; $R_3$ and $R_4$ are both ethyl; $R_5$ and $R_6$ are both —H; R and $R_2$ are both cyclopropyl; $R_3$ and $R_4$ are both methyl; $R_5$ is methyl; $R_6$ is —H; $R_1$ and $R_2$ are both 1-methylcyclopropyl; $R_3$ and $R_4$ are both methyl; $R_5$ and $R_6$ are both —H; $R_1$ and $R_2$ are both 1-methylcyclopropyl; $R_3$ and $R_4$ are both methyl; $R_5$ is methyl and $R_6$ is —H; $R_1$ and $R_2$ are both 1-methylcyclopropyl; $R_3$ and $R_4$ are both methyl; $R_5$ is ethyl and $R_6$ is —H; $R_1$ and $R_2$ are both 1-methylcyclopropyl; $R_3$ and $R_4$ are both methyl; $R_5$ is n-propyl and $R_6$ is —H; $R_1$ and $R_2$ are both 1-methylcyclopropyl; $R_3$ and $R_4$ are both methyl; $R_5$ and $R_6$ are both methyl; $R_1$ and $R_2$ are both 1-methylcyclopropyl; $R_3$ and $R_4$ are both ethyl; $R_5$ and $R_6$ are both —H; $R_1$ and $R_2$ are both 1-methylcyclopropyl; $R_3$ is methyl, and $R_4$ is ethyl; $R_5$ and $R_6$ are both —H; $R_1$ and $R_2$ are both 2-methylcyclopropyl; $R_3$ and $R_4$ are both methyl; $R_5$ and $R_6$ are both —H; $R_1$ and $R_2$ are both 2-phenylcyclopropyl; $R_3$ and $R_4$ are both methyl; $R_5$ and $R_6$ are both —H; $R_1$ and $R_2$ are both 1-phenylcyclopropyl; $R_3$ and $R_4$ are both methyl; $R_5$ and $R_6$ are both —H; $R_1$ and $R_2$ are both cyclobutyl; $R_3$ and $R_4$ are both methyl; $R_5$ and $R_6$ are both —H; $R_1$ and $R_2$ are both cyclopentyl; $R_3$ and $R_4$ are both methyl; $R_5$ and $R_6$ are both —H; $R_1$ and $R_2$ are both cyclohexyl; $R_3$ and $R_4$ are both methyl; $R_5$ and $R_6$ are both —H; $R_1$ and $R_2$ are both cyclohexyl; $R_3$ and $R_4$ are both phenyl; $R_5$ and $R_6$ are both —H; $R_1$ and $R_2$ are both methyl; $R_3$ and $R_4$ are both methyl; $R_5$ and $R_6$ are both —H; $R_1$ and $R_2$ are both methyl; $R_3$ and $R_4$ are both t-butyl; $R_5$ and $R_6$ are both —H; $R_1$ and $R_2$ are both methyl; $R_3$ and $R_4$ are both phenyl; $R_5$ and $R_6$ are both —H; $R_1$ and $R_2$ are both t-butyl; $R_3$ and $R_4$ are both methyl; $R_5$ and $R_6$ are both —H; $R_1$ and $R_2$ are ethyl; $R_3$ and $R_4$ are both methyl; $R_5$ and $R_6$ are both —H; $R_1$ and $R_2$ are both n-propyl; $R_3$ and $R_4$ are both methyl; $R_5$ and $R_6$ are both —H. In these examples, the pharmaceutically acceptable cation represented by $M^+$ and $M^{2+}$ is as described for Structural Formula (I), preferably $Li^+$, $Na^+$, $K^+$, $NH_3(C_2H_5OH)^+$ or $N(CH_3)_3(C_2H_5OH)^+$, more preferably $Na^+$ or $K^+$, even more preferably $Na^+$.

For many bis(thio-hydrazide amide) disalts represented by Structural Formula (II), Y is —$CH_2$—. Examples include wherein: $R_1$ and $R_2$ are both phenyl, and $R_3$ and $R_4$ are both o-$CH_3$-phenyl; $R_1$ and $R_2$ are both o—$CH_3C(O)O$-phenyl, and $R_3$ and $R_4$ are phenyl; $R_1$ and $R_2$ are both phenyl, and $R_3$ and $R_4$ are both methyl; $R_1$ and $R_2$ are both phenyl, and $R_3$ and $R_4$ are both ethyl; $R_1$ and $R_2$ are both phenyl, and $R_3$ and $R_4$ are both n-propyl; $R_1$ and $R_2$ are both p-cyanophenyl, and $R_3$ and $R_4$ are both methyl; $R_1$ and $R_2$ are both p-nitro phenyl, and $R_3$ and $R_4$ are both methyl; $R_1$ and $R_2$ are both 2,5-dimethoxyphenyl, and $R_3$ and $R_4$ are both methyl; $R_1$ and $R_2$ are both phenyl, and $R_3$ and $R_4$ are both n-butyl; $R_1$ and $R_2$ are both p-chlorophenyl, and $R_3$ and $R_4$ are both methyl; $R_1$ and $R_2$ are both 3-nitrophenyl, and $R_3$ and $R_4$ are both methyl; $R_1$ and $R_2$ are both 3-cyanophenyl, and $R_3$ and $R_4$ are both methyl; $R_1$ and $R_2$ are both 3-fluorophenyl, and $R_3$ and $R_4$ are both methyl; $R_1$ and $R_2$ are both 2-furanyl, and $R_3$ and $R_4$ are both phenyl; $R_1$ and $R_2$ are both 2-methoxyphenyl, and $R_3$ and $R_4$ are both methyl; $R_1$ and $R_2$ are both 3-methoxyphenyl, and $R_3$ and $R_4$ are both methyl; $R_1$ and $R_2$ are both 2,3-dimethoxyphenyl, and $R_3$ and $R_4$ are both methyl; $R_1$ and $R_2$ are both 2-methoxy-5-chlorophenyl, and $R_3$ and $R_4$ are both ethyl; $R_1$ and $R_2$ are both 2,5-difluorophenyl, and $R_3$ and $R_4$ are both methyl; $R_1$ and $R_2$ are both 2,5-dichlorophenyl, and $R_3$ and $R_4$ are both methyl; $R_1$ and $R_2$ are both 2,5-dimethylphenyl, and $R_3$ and $R_4$ are both methyl; $R_1$ and $R_2$ are both 2-methoxy-5-chlorophenyl, and $R_3$ and $R_4$ are both methyl; $R_1$ and $R_2$ are both 3,6-dimethoxyphenyl, and $R_3$ and $R_4$ are both methyl; $R_1$ and $R_2$ are both phenyl, and $R_3$ and $R_4$ are both 2-ethylphenyl; $R_1$ and $R_2$ are both 2-methyl-5-pyridyl, and $R_3$ and $R_4$ are both methyl; or $R_1$ is phenyl; $R_2$ is 2,5-dimethoxyphenyl, and $R_3$ and $R_4$ are both methyl; $R_1$ and $R_2$ are both methyl, and $R_3$ and $R_4$ are both p-$CF_3$-phenyl; $R_1$ and $R_2$ are both methyl, and $R_3$ and $R_4$ are both o-$CH_3$-phenyl; $R_1$ and $R_2$ are both -$CH_2)_3$COOH; and $R_3$ and $R_4$ are both phenyl; $R_1$ and $R_2$ are both represented by the following structural formula:

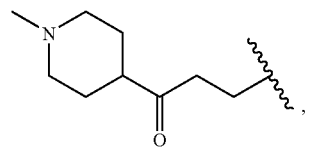

and $R_3$ and $R_4$ are both phenyl; $R_1$ and $R_2$ are both n-butyl, and $R_3$ and $R_4$ are both phenyl; $R_1$ and $R_2$ are both n-pentyl, $R_3$ and $R_4$ are both phenyl; $R_1$ and $R_2$ are both methyl, and $R_3$ and $R_4$ are both 2-pyridyl; $R_1$ and $R_2$ are both cyclohexyl, and $R_3$ and $R_4$ are both phenyl; $R_1$ and $R_2$ are both methyl, and $R_3$ and $R_4$ are both 2-ethylphenyl; $R_1$ and $R_2$ are both methyl, and $R_3$ and $R_4$ are both 2,6-dichlorophenyl; $R_1$-$R_4$ are all methyl; $R_1$ and $R_2$ are both methyl, and $R_3$ and $R_4$ are both t-butyl; $R_1$ and $R_2$ are both ethyl, and $R_3$ and $R_4$ are both methyl; $R_1$ and $R_2$ are both t-butyl, and $R_3$ and $R_4$ are both methyl; $R_1$ and $R_2$ are both cyclopropyl, and $R_3$ and $R_4$ are both methyl; $R_1$ and $R_2$ are both cyclopropyl, and $R_3$ and $R_4$ are both ethyl; $R_1$ and $R_2$ are both 1-methylcyclopropyl, and $R_3$ and $R_4$ are both methyl; $R_1$ and $R_2$ are both 2-methylcyclopropyl, and $R_3$ and $R_4$ are both methyl; $R_1$ and $R_2$ are both 1-phenylcyclopropyl, and $R_3$ and $R_4$ are both methyl; $R_1$ and $R_2$ are both 2-phenylcyclopropyl, and $R_3$ and $R_4$ are both methyl; $R_1$ and $R_2$ are both cyclobutyl, and $R_3$ and $R_4$ are both methyl; $R_1$ and $R_2$ are both cyclopentyl, and $R_3$ and $R_4$ are both methyl; $R_1$ is cyclopropyl, $R_2$ is phenyl, and $R_3$ and $R_4$ are both methyl. In these examples, the pharmaceutically acceptable cation represented by $M^+$ and $M^{2+}$ is as described for Structural Formula (I), preferably $Li^+$, $Na^+$, $K^+$, $NH_3(C_2H_5OH)^+$ or $N(CH_3)_3(C_2H_5OH)^+$, more preferably $Na^+$ or $K^+$, even more preferably $Na^+$.

Preferred examples of bis(thio-hydrazide amide) disalts of the present invention are the following:

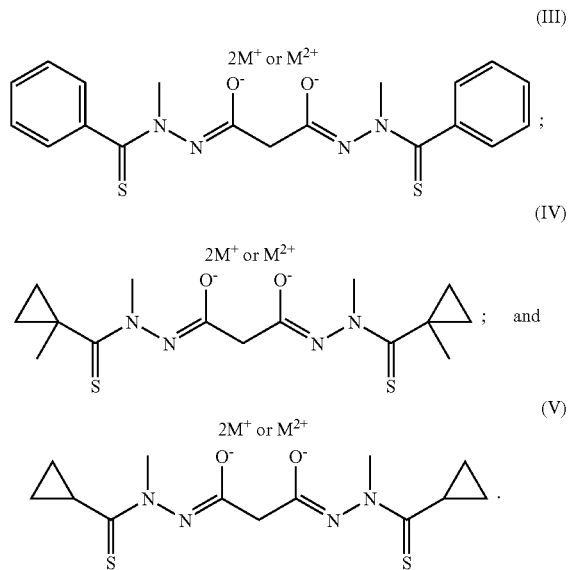

2 $M^+$ and $M^{2+}$ are as described above for Structural Formula (I). Preferably, the pharmaceutically acceptable cation is 2 $M^+$, wherein $M^+$ is $Li^+$, $Na^+$, $K^+$, $NH_3(C_2H_5OH)^+$ or $N(CH_3)_3(C_2H_5OH)^+$. More preferably, $M^+$ is $Na^+$ or $K^+$. Even more preferably, $M_+$ is $Na^+$.

In Structural Formulas (I)-(II), $R_1$ and $R_2$ are the same or different and/or $R_3$ and $R_4$ are the same or different. Preferably, $R_1$ and $R_2$ are the same and $R_3$ and $R_4$ are the same.

The disclosed bis(thio-hydrazide amide) disalts may have tautomeric forms. By way of example, tautomeric forms of the compounds represented by, for example, Structural Formula (II) wherein Y is —$CH_2$— are shown below:

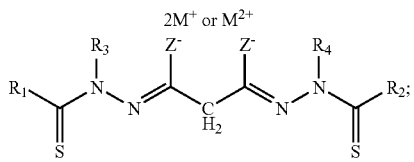

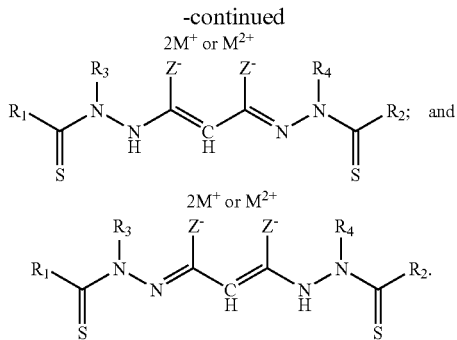

It is to be understood when one tautomeric form of a disclosed compound is depicted structurally, other tautomeric forms are also encompassed.

Certain compounds of the invention may be obtained as different stereoisomers (e.g., diastereomers and enantiomers). The invention includes all isomeric forms and racemic mixtures of the disclosed compounds and methods of treating a subject with both pure isomers and mixtures thereof, including racemic mixtures. Stereoisomers can be separated and isolated using any suitable method, such as chromatography.

A "straight chained hydrocarbyl group" is an alkylene group, i.e., —$(CH_2)_y$—, with one or more (preferably one) internal methylene groups optionally replaced with a linkage group. y is a positive integer (e.g., between 1 and 10), preferably between 1 and 6 and more preferably 1 or 2. A "linkage group" refers to a functional group which replaces a methylene in a straight chained hydrocarbyl. Examples of suitable linkage groups include a ketone (—C(O)—), alkene, alkyne, phenylene, ether (—O—), thioether (—S—), or amine (—N($R^a$)—), wherein $R^a$ is defined below. A preferred linkage group is —C($R_5R_6$)—, wherein $R_5$ and $R_6$ are defined above. Suitable substituents for an alkylene group and a hydrocarbyl group are those which do not substantially interfere with the anti-cancer activity of the disclosed compounds. $R_5$ and $R_6$ are preferred substituents for an alkylene or hydrocarbyl group represented by Y.

An aliphatic group is a straight chained, branched or cyclic non-aromatic hydrocarbon which is completely saturated or which contains one or more units of unsaturation. Typically, a straight chained or branched aliphatic group has from 1 to about 20 carbon atoms, preferably from 1 to about 10, and a cyclic aliphatic group has from 3 to about 10 carbon atoms, preferably from 3 to about 8. An aliphatic group is preferably a straight chained or branched alkyl group, e.g, methyl, ethyl, n-propyl, iso-propyl, n-butyl, sec-butyl, tert-butyl, pentyl, hexyl, pentyl or octyl, or a cycloalkyl group with 3 to about 8 carbon atoms. A C1-C8 straight chained or branched alkyl group or a C3-C8 cyclic alkyl group is also referred to as a "lower alkyl" group.

The term "aromatic group" may be used interchangeably with "aryl," "aryl ring," "aromatic ring," "aryl group" and "aromatic group." Aromatic groups include carbocyclic aromatic groups such as phenyl, naphthyl, and anthracyl, and heteroaryl groups such as imidazolyl, thienyl, furanyl, pyridyl, pyrimidy, pyranyl, pyrazolyl, pyrroyl, pyrazinyl, thiazole, oxazolyl, and tetrazole. The term "heteroaryl group" may be used interchangeably with "heteroaryl," "heteroaryl ring," "heteroaromatic ring" and "heteroaromatic group." Heteroaryl groups are aromatic groups that comprise one or more heteroatom, such as sulfur, oxygen and nitrogen, in the ring structure. Preferably, heteroaryl groups comprise from one to four heteroatoms.

Aromatic groups also include fused polycyclic aromatic ring systems in which a carbocyclic aromatic ring or heteroaryl ring is fused to one or more other heteroaryl rings. Examples include benzothienyl, benzofuranyl, indolyl, quinolinyl, benzothiazole, benzooxazole, benzimidazole, quinolinyl, isoquinolinyl and isoindolyl.

The term "arylene" refers to an aryl group which is connected to the remainder of the molecule by two other bonds. By way of example, the structure of a 1,4-phenylene group is shown below:

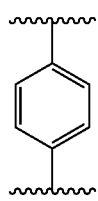

Substituents for an arylene group are as described below for an aryl group.

Non-aromatic heterocyclic rings are non-aromatic rings which include one or more heteroatoms such as nitrogen, oxygen or sulfur in the ring. The ring can be five, six, seven or eight-membered. Preferably, heterocyclic groups comprise from one to about four heteroatoms. Examples include tetrahydrofuranyl, tetrahyrothiophenyl, morpholino, thiomorpholino, pyrrolidinyl, piperazinyl, piperidinyl, and thiazolidinyl.

Suitable substituents on an aliphatic group (including an alkylene group), non-aromatic heterocyclic group, benzylic or aryl group (carbocyclic and heteroaryl) are those which do not substantially interfere with the anti-cancer activity of the disclosed compounds. A substituent substantially interferes with anti-cancer activity when the anti-cancer activity is reduced by more than about 50% in a compound with the substituent compared with a compound without the substituent. Examples of suitable substituents include —$R^a$, —OH, —Br, —Cl, I, —F, —$OR^a$, —O—$COR^a$, —$COR^a$, —CN, —$NO_2$, —COOH, —$SO_3H$, —$NH_2$, —$NHR^a$, —$N(R^aR^b)$, —$COOR^a$, —CHO, —$CONH_2$, —$CONHR^a$, —CON$(R^aR^b)$, —$NHCOR^a$, —$NR^cCOR^a$, —$NHCONH_2$, —NHCON$R^aH$, —NHCON$(R^aR^b)$, —$NR^cCONH_2$, —$NR^cCON$-$R^aH$, —$NR^cCON(R^aR^b)$, —C(=NH)—$NH_2$, —C(=NH)—$NHR^a$, —C(=NH)—$N(R^aR^b)$, —C(=$NR^c$)—$NH_2$, —C(=$NR^c$)—$NHR^a$, —C(=$NR^c$)—$N(R^aR^b)$, —NH—C(=NH)—$NH_2$, —NH—C(=NH)—$NHR^a$, —NH—C(=NH)—$N(R^aR^b)$, —NH—C(=$NR^c$)—$NH_2$, —NH—C(=$NR^c$)—$NHR^a$, —NH—C(=$NR^c$)—$N(R^aR^b)$, —$NR^dH$—C(=NH)—$NH_2$, —$NR^d$—C(=NH)—$NHR^a$, —$NR^d$—C(=NH)—$N(R^aR^b)$, —$NR^d$—C(=$NR^c$)—$NH_2$, —$NR^d$—C(=$NR^c$)—$NHR^a$, —$NR^d$—C(=$NR^c$)—N$(R^aR^b)$, —$NHNH_2$, —$NHNHR^a$, —$NHR^aR^b$, —$SO_2NH_2$, —$SO_2NHR^a$, —$SO_2NR^aR^b$, —CH=$CHR^a$, —CH=$CR^aR^b$, —$CR^c$=$CR^aR^b$,—$CR^c$=$CHR^a$, —$CR^c$=$CR^aR^b$, —$CCR^a$, —SH, —$SR^a$, —S(O)$R^a$, —S(O)$_2R^a$.

$R^a$—$R^d$ are each independently an alkyl group, aromatic group, non-aromatic heterocyclic group or —$N(R^aR^b)$, taken together, form a substituted or unsubstituted non-aromatic heterocyclic group. The alkyl, aromatic and non-aromatic heterocyclic group represented by $R^a$—$R^d$ and the non-aromatic heterocyclic group represented by —$N(R^aR^b)$ are each optionally and independently substituted with one or more groups represented by $R^\#$.

$R^\#$ is $R^+$, —$OR^+$, —O(haloalkyl), —$SR^+$, —$NO_2$, —CN, —NCS, —$N(R^+)_2$, —$NHCO_2R^+$, —NHC(O)$R^+$, —NHNHC(O)$R^+$, —NHC(O)N$(R^+)_2$, —NHNHC(O)N$(R^+)_2$, —$NHNHCO_2R^+$, —C(O)C(O)$R^+$, —C(O)$CH_2$C(O)$R^+$, —$CO_2R^+$, —C(O)$R^+$, —C(O)N$(R^+)_2$, —OC(O)$R^+$, —OC(O)N$(R^+)_2$, —S(O)$_2R^+$, —$SO_2$N$(R^+)_2$, —S(O)$R^+$, —$NHSO_2$N$(R^+)_2$, —$NHSO_2R^+$, —C(=S)N$(R^+)_2$, or —C(=NH)—N$(R^+)_2$.

$R^+$is —H, a C1-C4 alkyl group, a monocyclic heteroaryl group, a non-aromatic heterocyclic group or a phenyl group optionally substituted with alkyl, haloalkyl, alkoxy, haloalkoxy, halo, —CN, —$NO_2$, amine, alkylamine or dialkylamine. Optionally, the group —N$(R^+)_2$ is a non-aromatic heterocyclic group, provided that non-aromatic heterocyclic groups represented by $R^+$ and —N$(R^+)_2$ that comprise a secondary ring amine are optionally acylated or alkylated.

Preferred substituents for a phenyl group, including phenyl groups represented by $R_1$-$R_4$, include C1-C4 alkyl, C1-C4 alkoxy, C1-C4 haloalkyl, C1-C4 haloalkoxy, phenyl, benzyl, pyridyl, —OH, —$NH_2$, —F, —Cl, —Br, —I, —$NO_2$ or —CN.

Preferred substituents for a cycloalkyl group, including cycloalkyl groups represented by $R_1$ and $R_2$, are alkyl groups, such as a methyl or ethyl group.

Another embodiment of the present invention is a pharmaceutical composition comprising a bis(thio-hydrazide amide) disalt disclosed herein and a pharmaceutically acceptable carrier or diluent.

Suitable pharmaceutically acceptable carriers may contain inert ingredients which do not inhibit the biological activity of the disclosed disalts. The pharmaceutically acceptable carriers should be biocompatible, i.e., non-toxic, non-inflammatory, non-immunogenic and devoid of other undesired reactions upon the administration to a subject. Standard pharmaceutical formulation techniques can be employed, such as those described in Remington's Pharmaceutical Sciences, Mack Publishing Company, Easton, Pa. Formulation of the compound to be administered will vary according to the route of administration selected (e.g., solution, emulsion, capsule). Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextrins) are known in the art (Baker, et al., "Controlled Release of Biological Active Agents", John Wiley and Sons, 1986).

Another embodiment of the present invention is a method of treating a subject with a cancer. Optionally, the method of the invention can be used for a multi-drug resistant cancer as described below. The method comprises the step of administering an effective amount of a bis(thio-hydrazide amide) disalt described herein. Preferably, one or more additional anti-cancer drugs are co-administered with the bis(thio-hydrazide amide) disalt. Examples of anti-cancer drugs are described below. Preferably, the co-administered anti-cancer drug is an agent that stabilizes mictotubules, such as paclitaxel or an analog of paclitaxel.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

As noted above, one embodiment of the present invention is directed to treating subjects with a cancer. "Treating a subject with a cancer" includes achieving, partially or substantially, one or more of the following: arresting the growth or spread of a cancer, reducing the extent of a cancer (e.g., reducing size of a tumor or reducing the number of affected sites), inhibiting the growth rate of a cancer, and ameliorating or improving a clinical symptom or indicator associated with a cancer (such as tissue or serum components).

Cancers that can be treated or prevented by the methods of the present invention include, but are not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrobm's macroglobulinemia, and heavy chain disease.

Other examples of leukemias include acute and/or chronic leukemias, e.g., lymphocytic leukemia (e.g., as exemplified by the p388 (murine) cell line), large granular lymphocytic leukemia, and lymphoblastic leukemia; T-cell leukemias, e.g., T-cell leukemia (e.g., as exemplified by the CEM, Jurkat, and HSB-2 (acute), YAC-1(murine) cell lines), T-lymphocytic leukemia, and T-lymphoblastic leukemia; B cell leukemia (e.g., as exemplified by the SB (acute) cell line), and B-lymphocytic leukemia; mixed cell leukemias, e.g., B and T cell leukemia and B and T lymphocytic leukemia; myeloid leukemias, e.g., granulocytic leukemia, myelocytic leukemia (e.g., as exemplified by the HL-60 (promyelocyte) cell line), and myelogenous leukemia (e.g., as exemplified by the K562 (chronic)cell line); neutrophilic leukemia; eosinophilic leukemia; monocytic leukemia (e.g., as exemplified by the THP-1(acute) cell line); myelomonocytic leukemia; Naegeli-type myeloid leukemia; and nonlymphocytic leukemia. Other examples of leukemias are described in Chapter 60 of *The Chemotherapy Sourcebook*, Michael C. Perry Ed., Williams & Williams (1992) and Section 36 of *Holland Frie Cancer Medicine* 5th Ed., Bast et al. Eds., B.C. Decker Inc. (2000). The entire teachings of the preceding references are incorporated herein by reference.

In one embodiment, the disclosed method is believed to be particularly effective in treating a subject with non-solid tumors such as multiple myeloma. In another embodiment, the disclosed method is believed to be particularly effective against T-leukemia (e.g., as exemplified by Jurkat and CEM cell lines); B-leukemia (e.g., as exemplified by the SB cell line); promyelocytes (e.g., as exemplified by the HL-60 cell line); uterine sarcoma (e.g., as exemplified by the MES-SA cell line); monocytic leukemia (e.g., as exemplified by the THP-1(acute) cell line); and lymphoma (e.g., as exemplified by the U937 cell line); most preferably, this embodiment of the method employs the disodium salt of Compound (1).

The disclosed method is particularly effective at treating subjects whose cancer has become "multi-drug resistant". A cancer which initially responded to an anti-cancer drug becomes resistant to the anti-cancer drug when the anti-cancer drug is no longer effective in treating the subject with the cancer. For example, many tumors will initially respond to treatment with an anti-cancer drug by decreasing in size or even going into remission, only to develop resistance to the drug. Drug resistant tumors are characterized by a resumption of their growth and/or reappearance after having seemingly gone into remission, despite the administration of increased dosages of the anti-cancer drug. Cancers that have developed resistance to two or more anti-cancer drugs are said to be "multi-drug resistant". For example, it is common for cancers to become resistant to three or more anti-cancer agents, often five or more anti-cancer agents and at times ten or more anti-cancer agents.

An "effective amount" is the quantity of compound in which a beneficial clinical outcome is achieved when the compound is administered to a subject with a cancer. A "beneficial clinical outcome" includes a reduction in tumor mass, a reduction in metastasis, a reduction in the severity of the symptoms associated with the cancer and/or an increase in the longevity of the subject compared with the absence of the treatment. The precise amount of compound administered to a subject will depend on the type and severity of the disease or condition and on the characteristics of the subject, such as general health, age, sex, body weight and tolerance to drugs. It will also depend on the degree, severity and type of cancer. The skilled artisan will be able to determine appropriate dosages depending on these and other factors. Effective amounts of the disclosed compounds typically range between about 1 mg/mm$^2$ per day and about 10 grams/mm$^2$ per day, and preferably between 10 mg/mm$^2$ per day and about 5 grams/mm$^2$. When co-administered with another anti-cancer agent, an "effective amount" of the second anti-cancer agent will depend on the type of drug used. Suitable dosages are known for approved anti-cancer agents and can be adjusted by the skilled artisan according to the condition of the subject, the type of cancer being treated and the amount of bis(thio-hydrazide amide) disalt being used.

The disclosed bis(thio-hydrazide amide) disalts are administered by any suitable route, including, for example, orally in capsules, suspensions or tablets or by parenteral administration. Parenteral administration can include, for example, systemic administration, such as by intramuscular, intravenous, subcutaneous, or intraperitoneal injection. The bis(thio-hydrazide amide) disalts can also be administered orally (e.g., dietary), topically, by inhalation (e.g., intrabronchial, intranasal, oral inhalation or intranasal drops), or rectally, depending on the type of cancer to be treated. Oral and parenteral administrations are preferred modes of administration.

Optionally, the disclosed bis(thio-hydrazide amide) disalts can be co-administered with other anti-cancer agents such as Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan;

cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A;

placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin.

Examples of therapeutic antibodies that can be used include but are not limited to HERCEPTIN® (Trastuzumab) (Genentech, CA) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); LYMPHOCIDE™ Y-90 (Immunomedics); Lymphoscan (Tc-99m-labeled; radioimaging; Immunomedics); Nuvion (against CD3; Protein Design Labs); CM3 is a humanized anti-ICAM3 antibody (ICOS Pharm); IDEC-114 is a primatied anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CAT/BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CD20-sreptavidin (+biotin-yttrium 90; NeoRx); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); and CAT-152 is a human anti-TGF-β2 antibody (Cambridge Ab Tech).

Chemotherapeutic agents that can be used in the methods and compositions of the invention include but are not limited to alkylating agents, antimetabolites, natural products, or hormones. Examples of alkylating agents useful for the treatment or prevention of T-cell malignancies in the methods and compositions of the invention include but are not limited to, nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites useful for the treatment or prevention of T-cell malignancies in the methods and compositions of the invention include but are not limited to folic acid analog (e.g., methotrexate), or pyrimidine analogs (e.g., Cytarabine), purine analogs (e.g., mercaptopurine, thioguanine, pentostatin). Examples of natural products useful for the treatment or prevention of T-cell malignancies in the methods and compositions of the invention include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents useful for the treatment or prevention of cancer in the methods and compositions of the invention include but are not limited to, nitrogen mustards (e.g., mechloroethamine, cyclophosphamide, chlorambucil, melphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites useful for the treatment or prevention of cancer in the methods and compositions of the invention include but are not limited to folic acid analog (e.g., methotrexate), or pyrimidine analogs (e.g., fluorouracil, floxouridine, Cytarabine), purine analogs (e.g., mercaptopurine, thioguanine, pentostatin). Examples of natural products useful for the treatment or prevention of cancer in the methods and compositions of the invention include but are not limited to vinca alkaloids (e.g., vinblastin, vincristine), epipodophyllotoxins (e.g., etoposide, teniposide), antibiotics (e.g., actinomycin D, daunorubicin, doxorubicin, bleomycin, plicamycin, mitomycin), enzymes (e.g., L-asparaginase), or biological response modifiers (e.g., interferon alpha). Examples of hormones and antagonists useful for the treatment or prevention of cancer in the methods and compositions of the invention include but are not limited to adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and with the compositions of the invention for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

The bis(thio-hydrazide amide) disalts disclosed herein are believed to be particularly effective when co-administered with anti-cancer agents which act by arresting cells in the G2-M phases due to stabilization of microtubules. Thus, the disclosed method preferably includes co-administration of anti-cancer drugs which act by this mechanism. Examples of anti-cancer agents which act by arresting cells in the G2-M phases due to stabilization of microtubules include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B ), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-IAABE (Cytoskeleton/Mt. Sinai School of Medicine), A-204197 (Abbott), T-607 (Tularik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-0Y-007 (National Health Research Institutes), and SSR-250411 (Sanofi), and Hsp90 inhibitors such as geldanmycin, radicicol, herbimycin A, macbecin I and II, novobiocin, 17-Allylamino-17-demethoxygeldanamycin (17AAG), 17-Demethoxy-17-[2-(dimethylamino)ethylamino]geldanamycin (17DMAG), CNF-1010, purine-based Hsp90 inhibitors such as PU3, PU24FCl, and PU29FCl, and oxime derivatives of radicicol such as KF25706 and KF58333.

Figure 2:
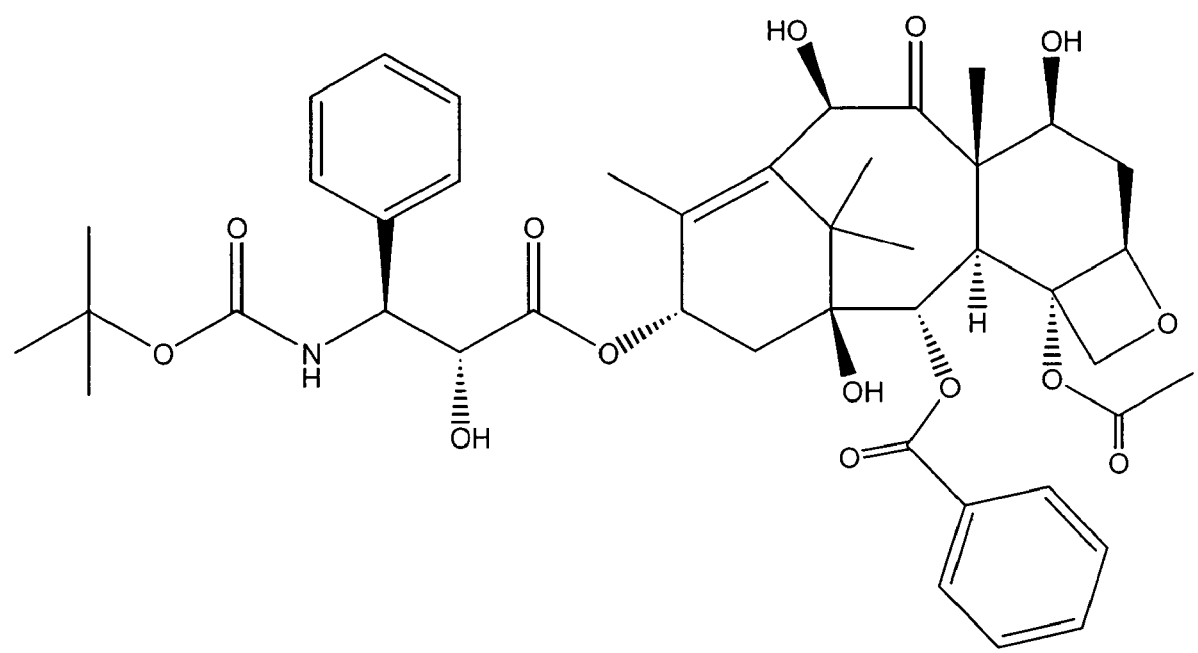
FIG. 2 is the structure of docetaxel (TAXOTERE).
Figure 3:
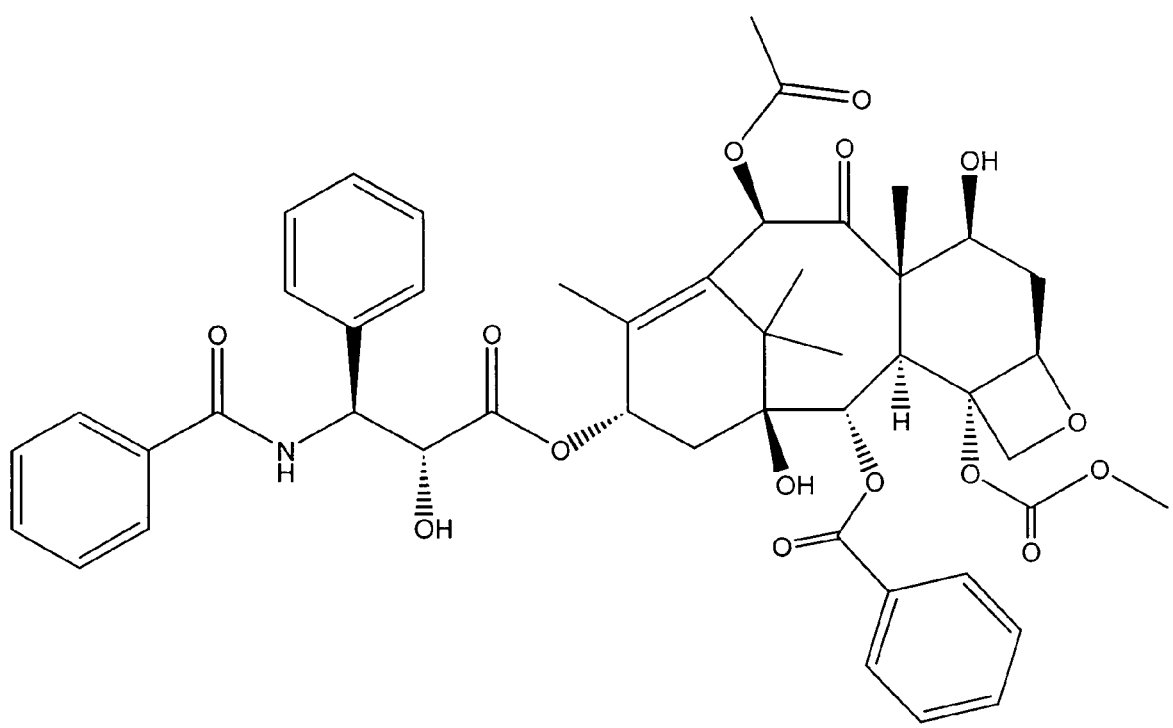
FIGS. 3-23 are each the structure of a paclitaxel analog.
Figure 4:
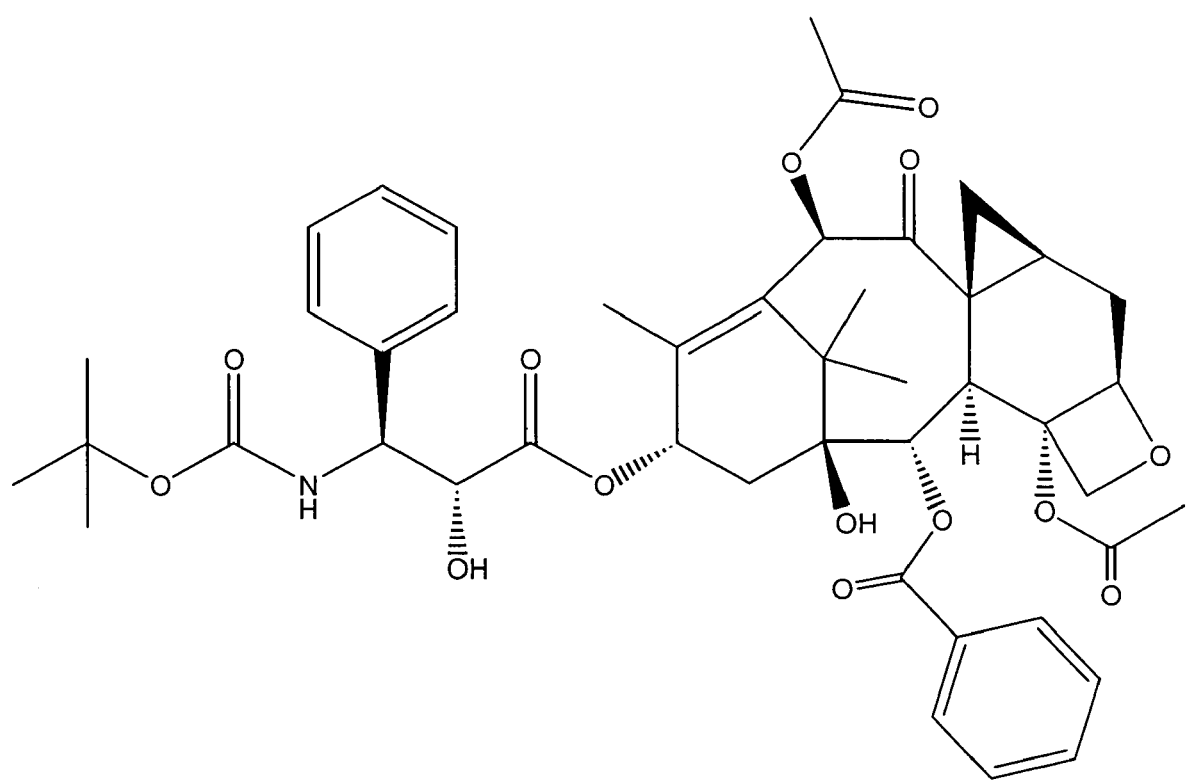
Figure 5:
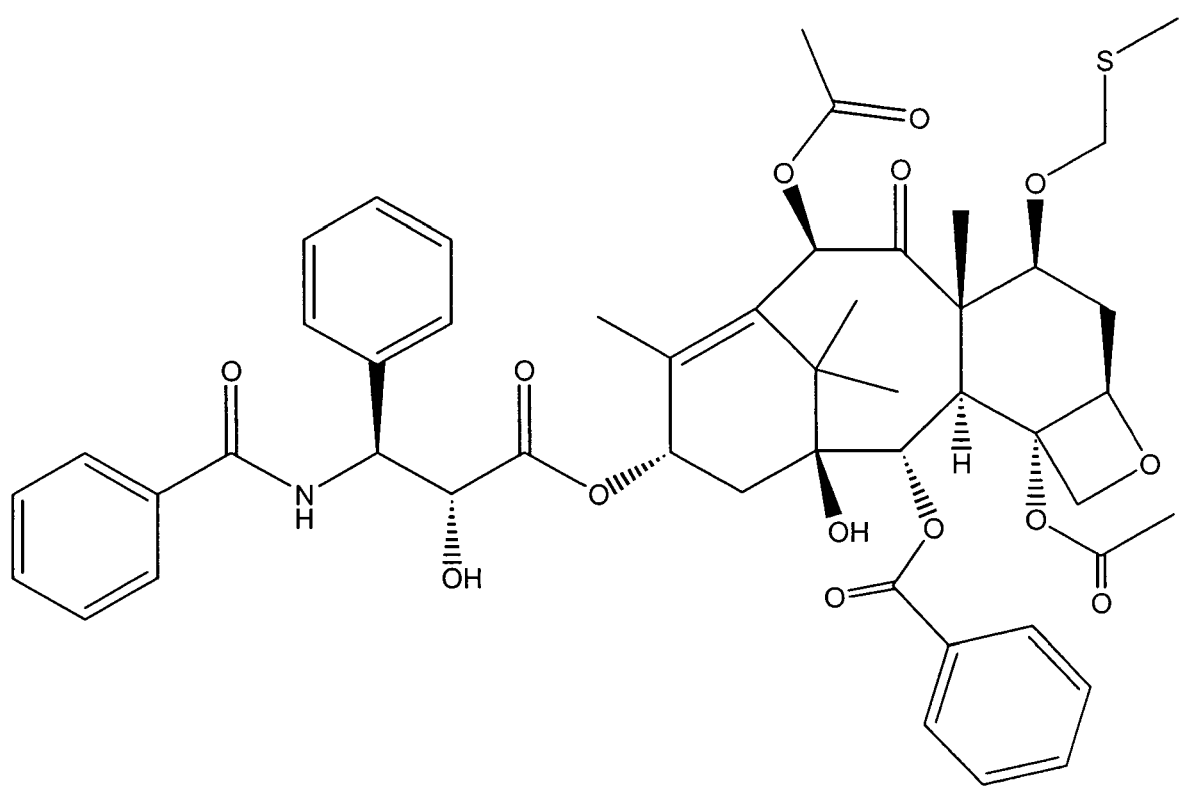
Figure 6:
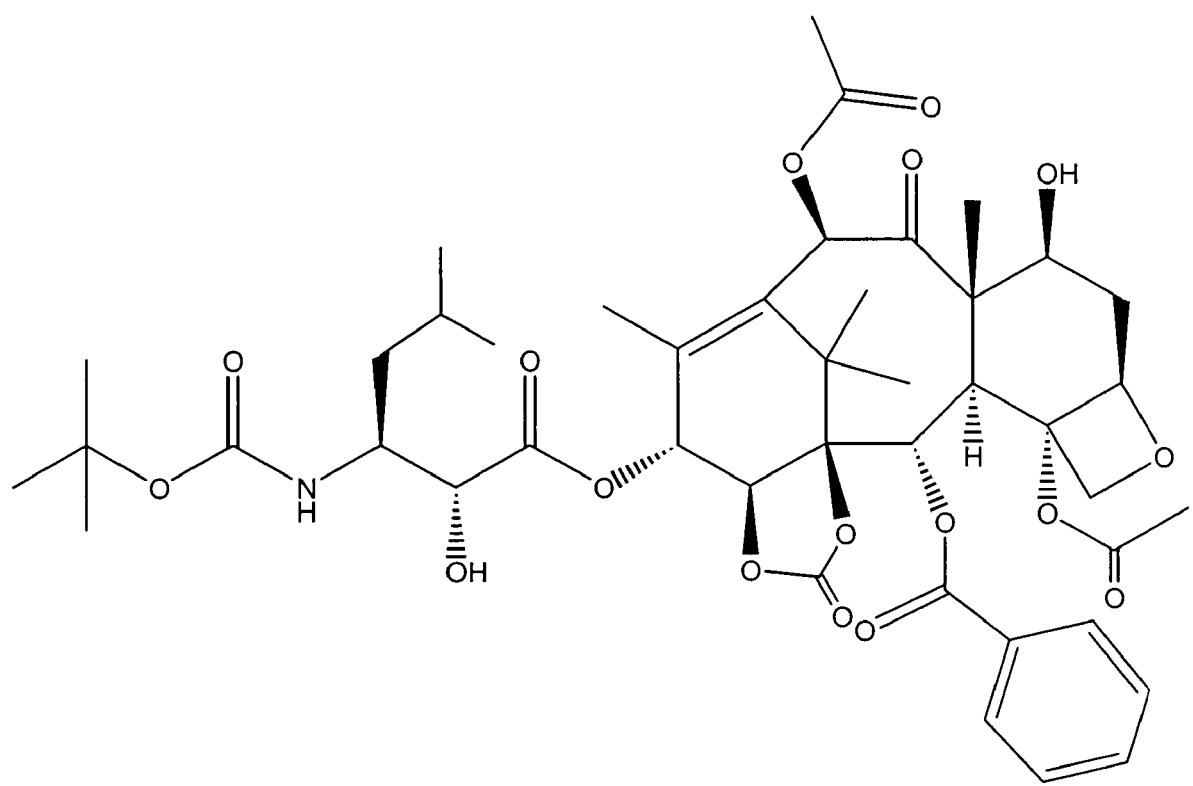
Figure 7:
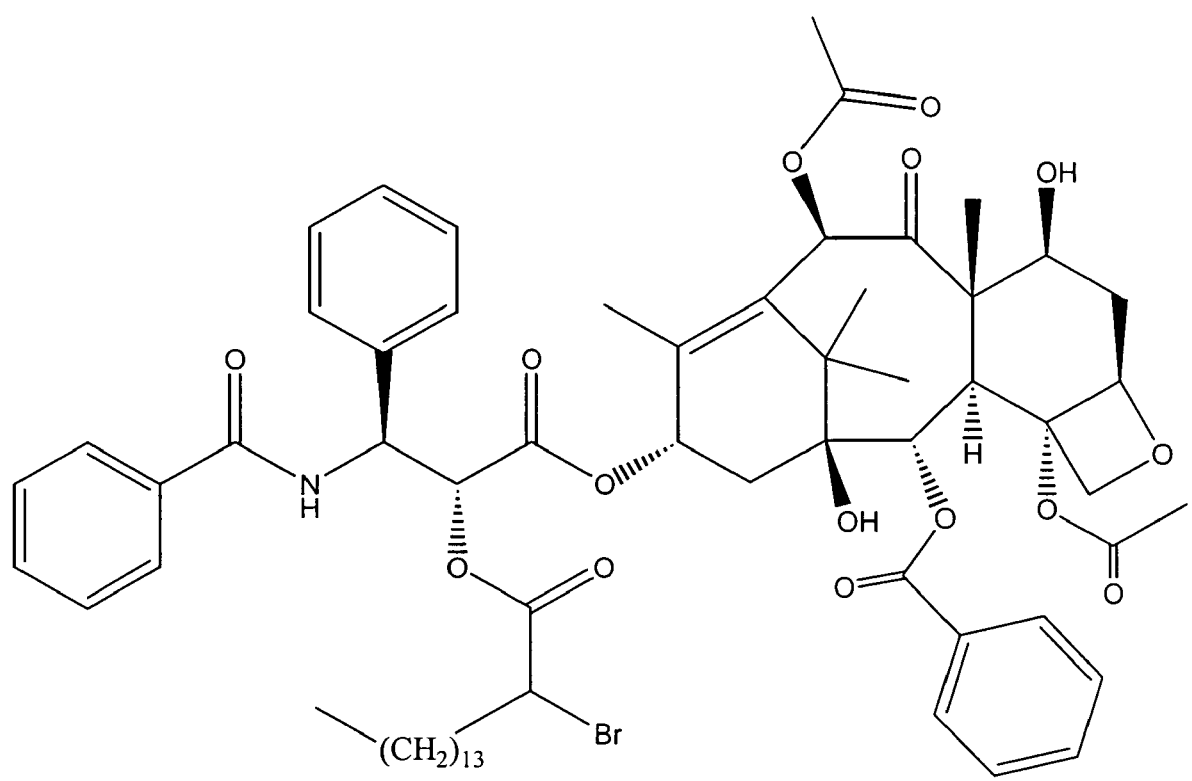
Figure 8:
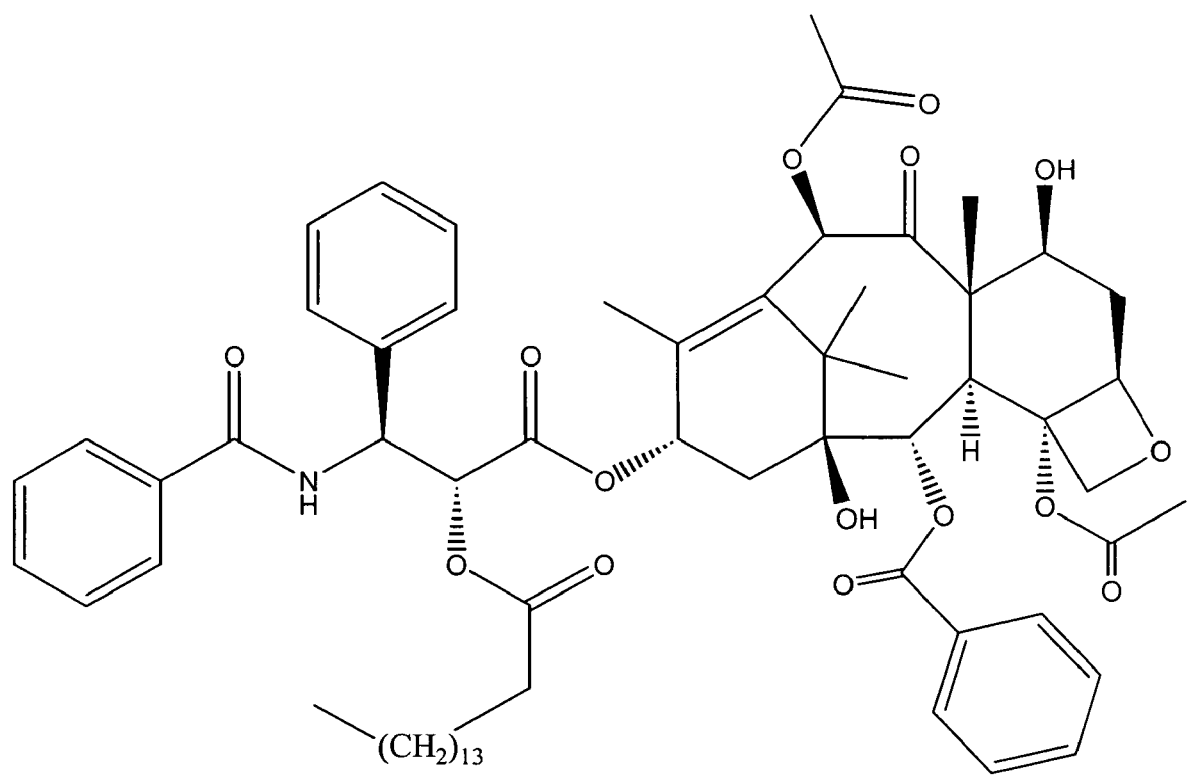
Figure 9:
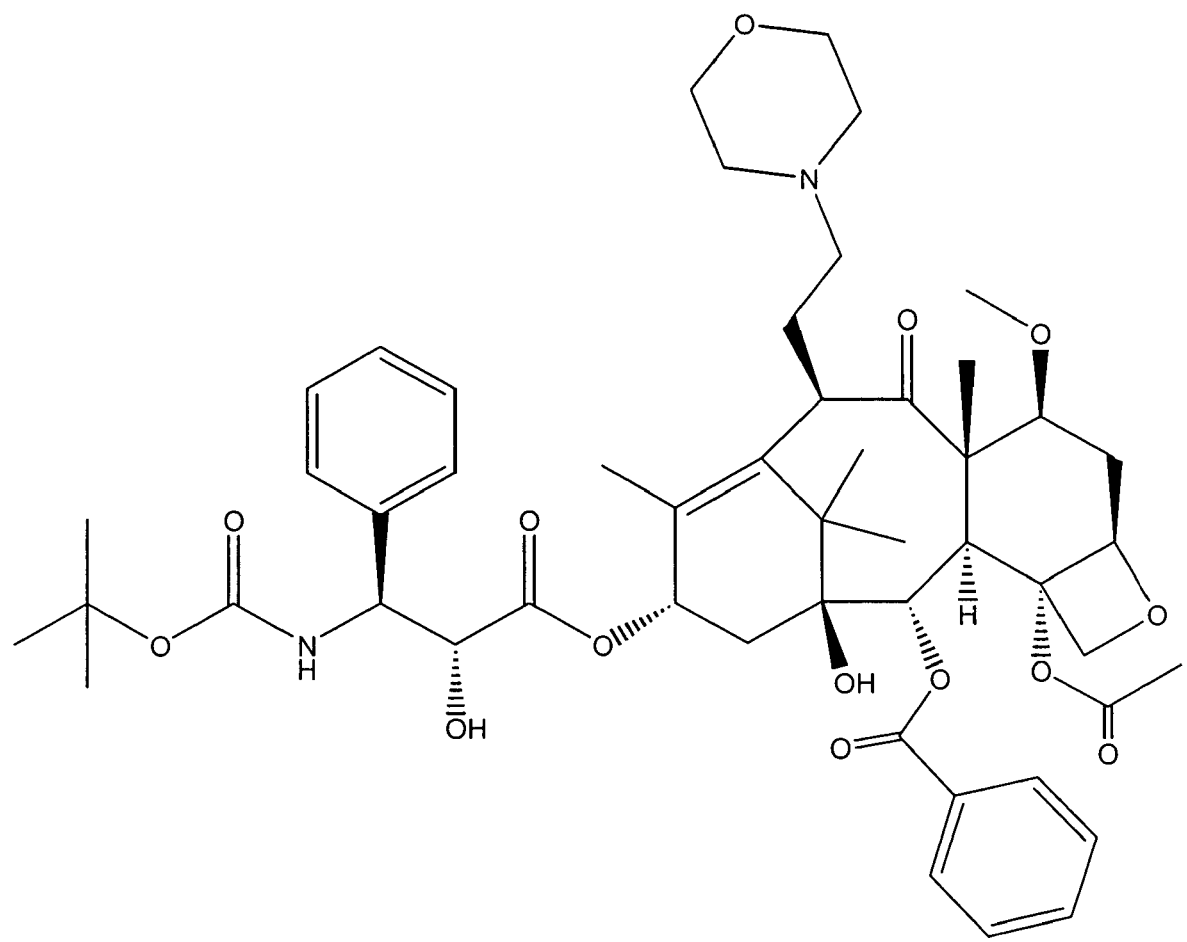
Figure 10:
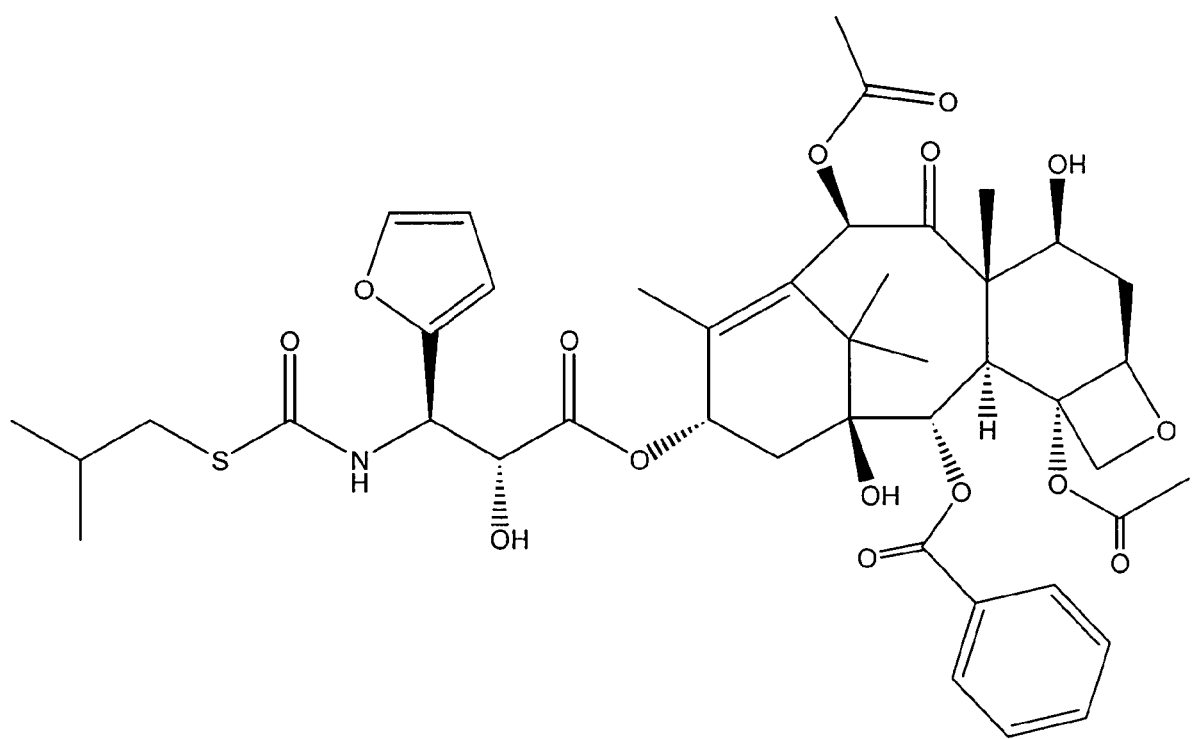
Figure 11:
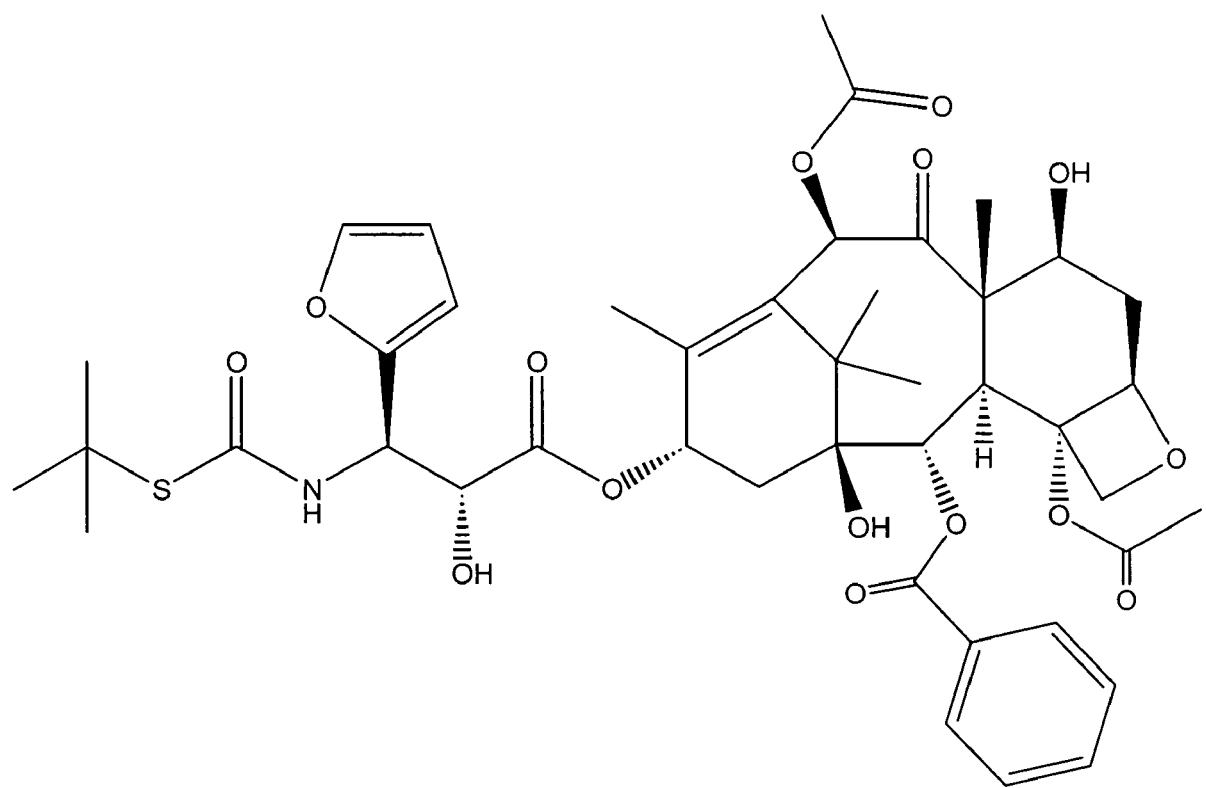
Figure 12:
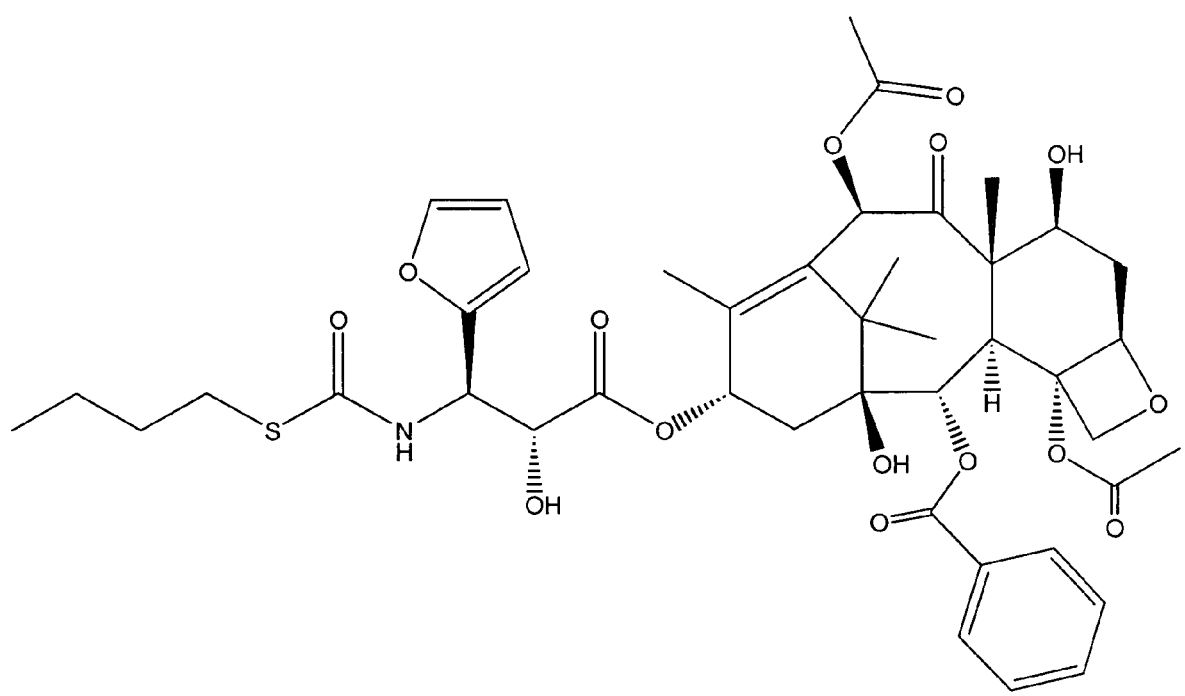
Figure 13:
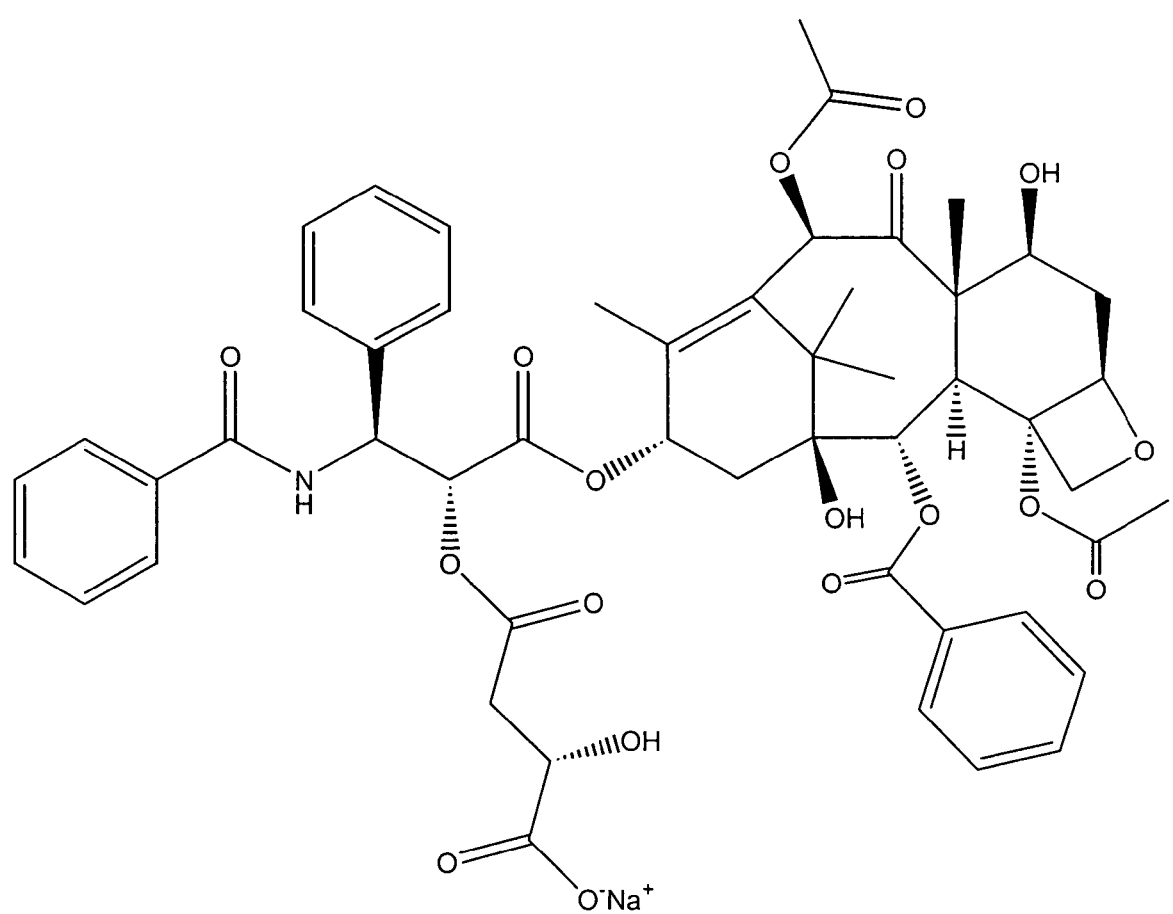
Figure 14:
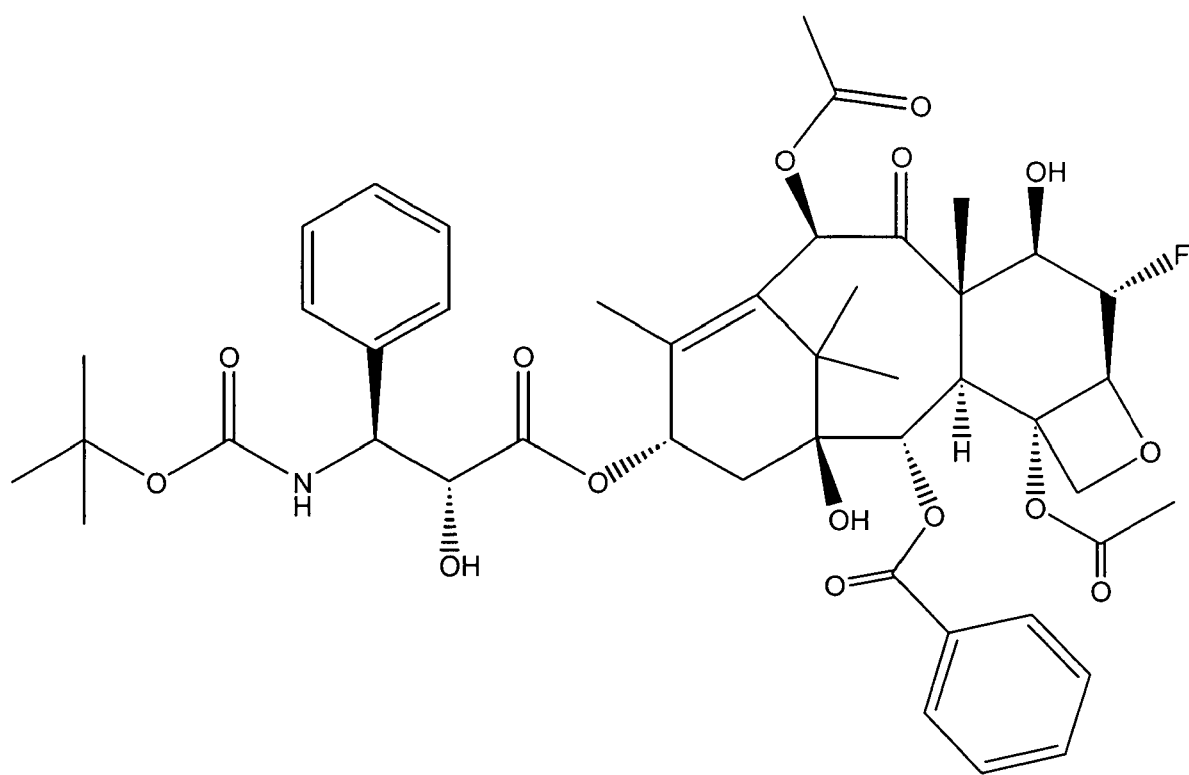
Figure 15:
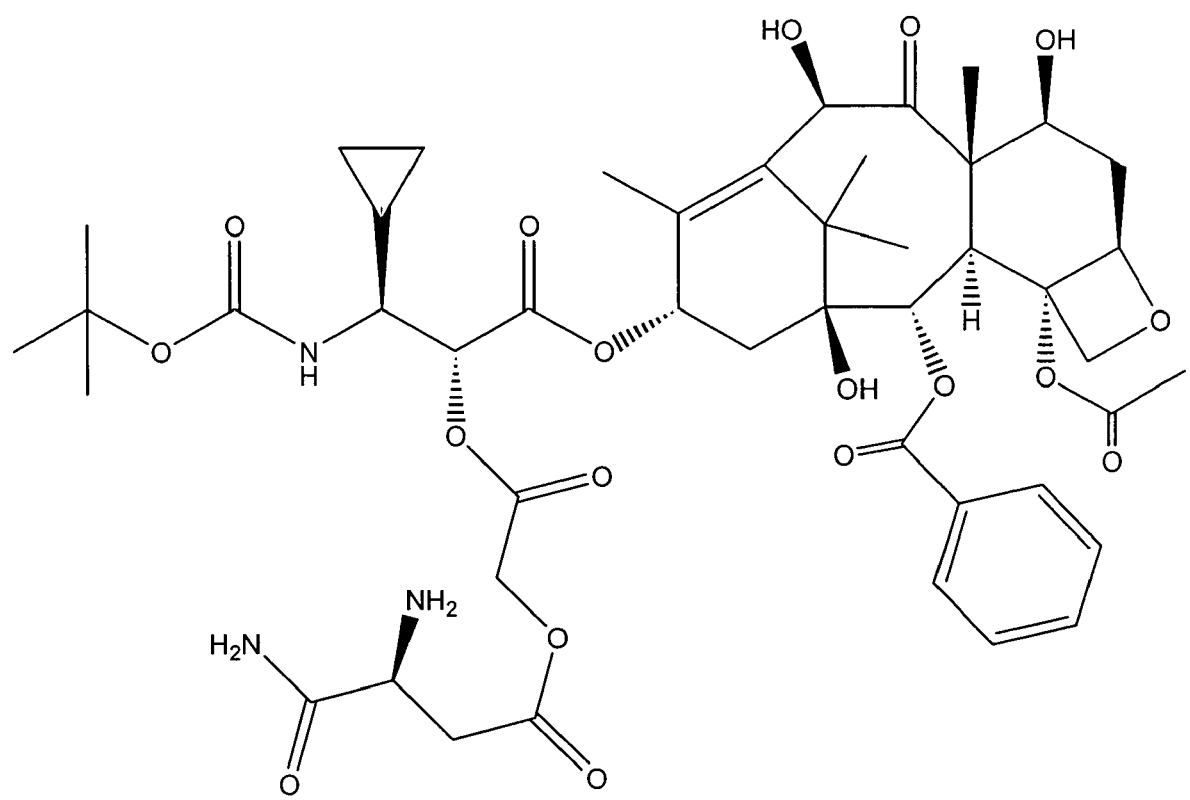
Figure 16:
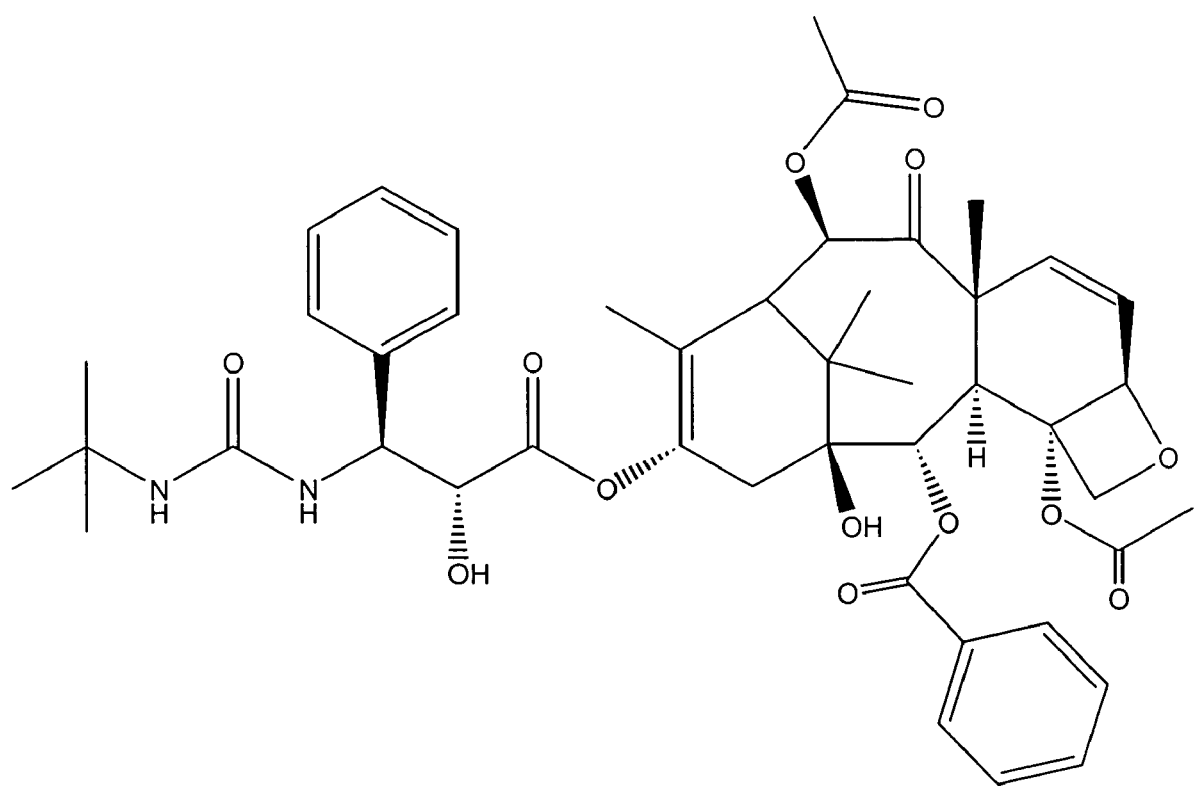
Figure 17:
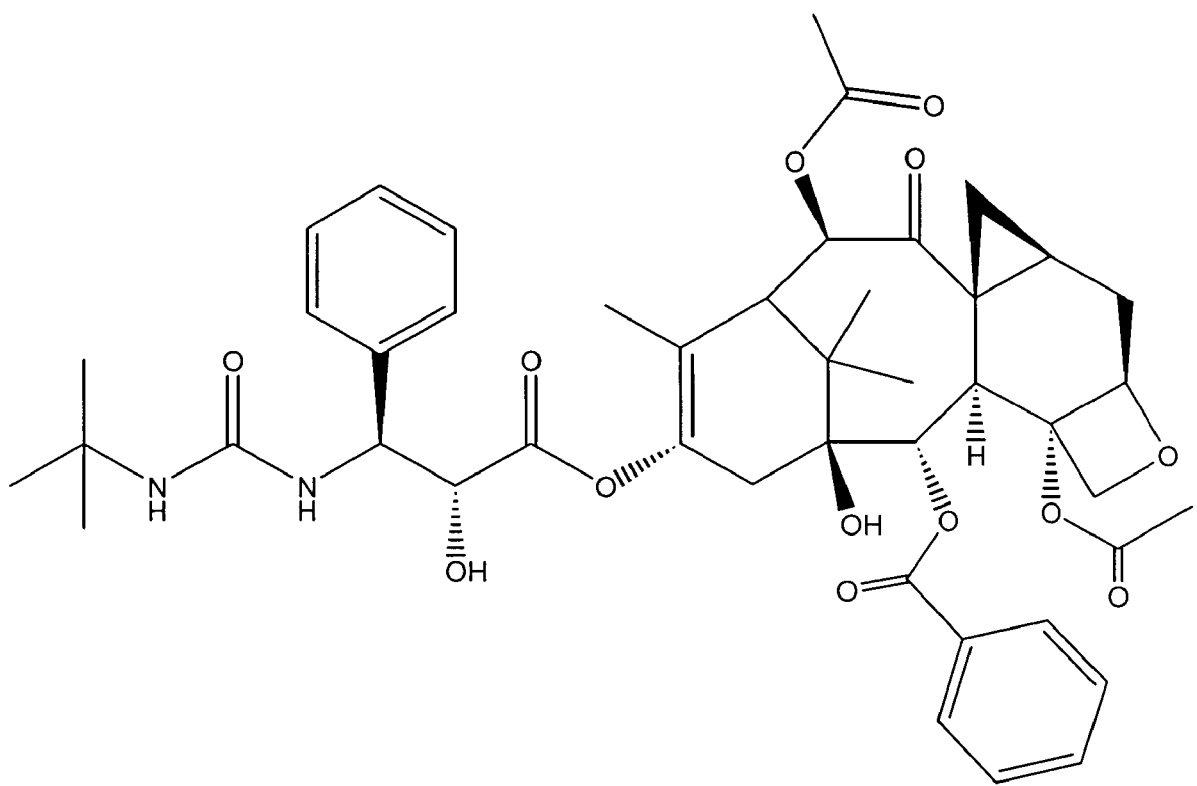
Figure 18:
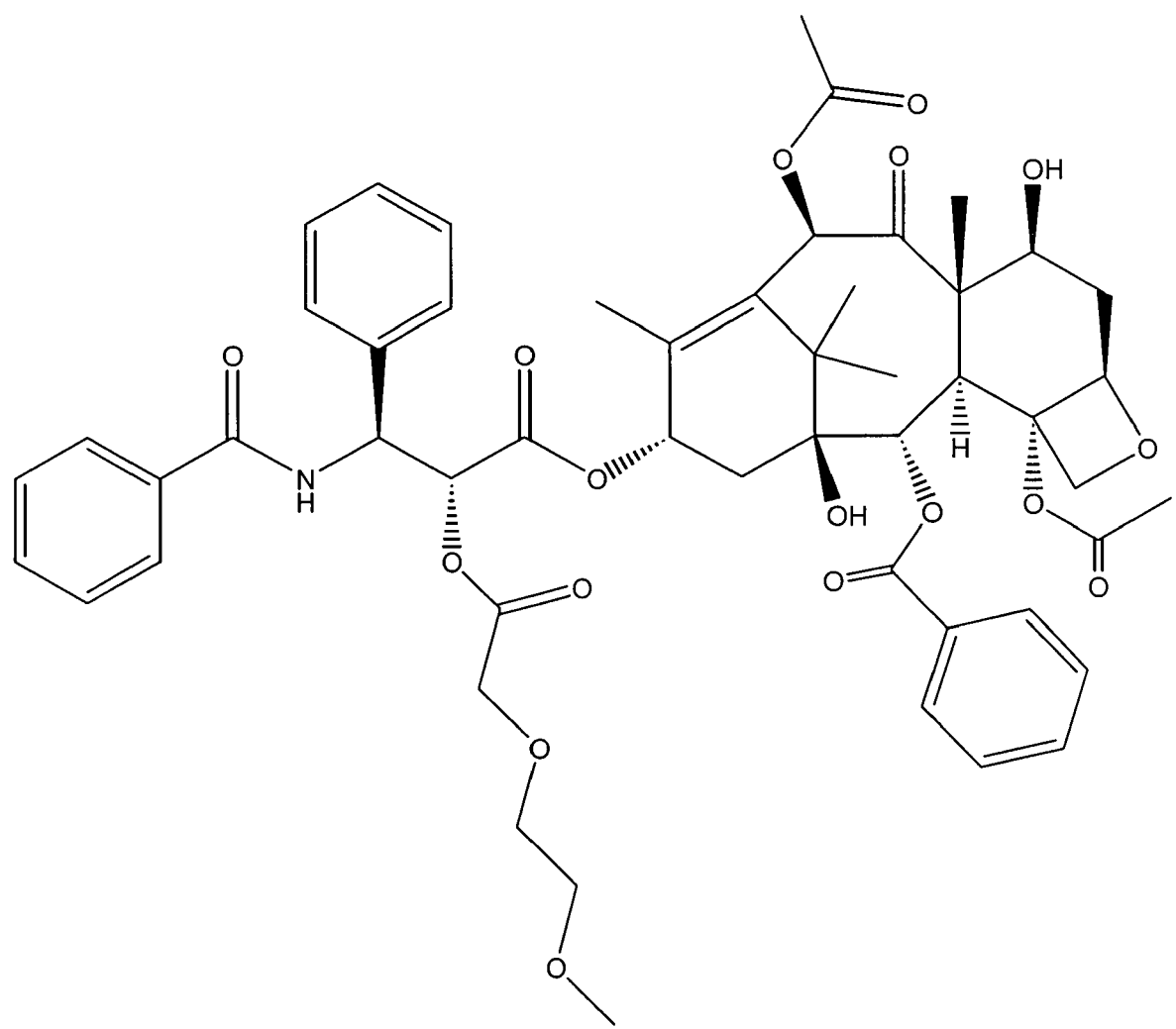
Figure 19:
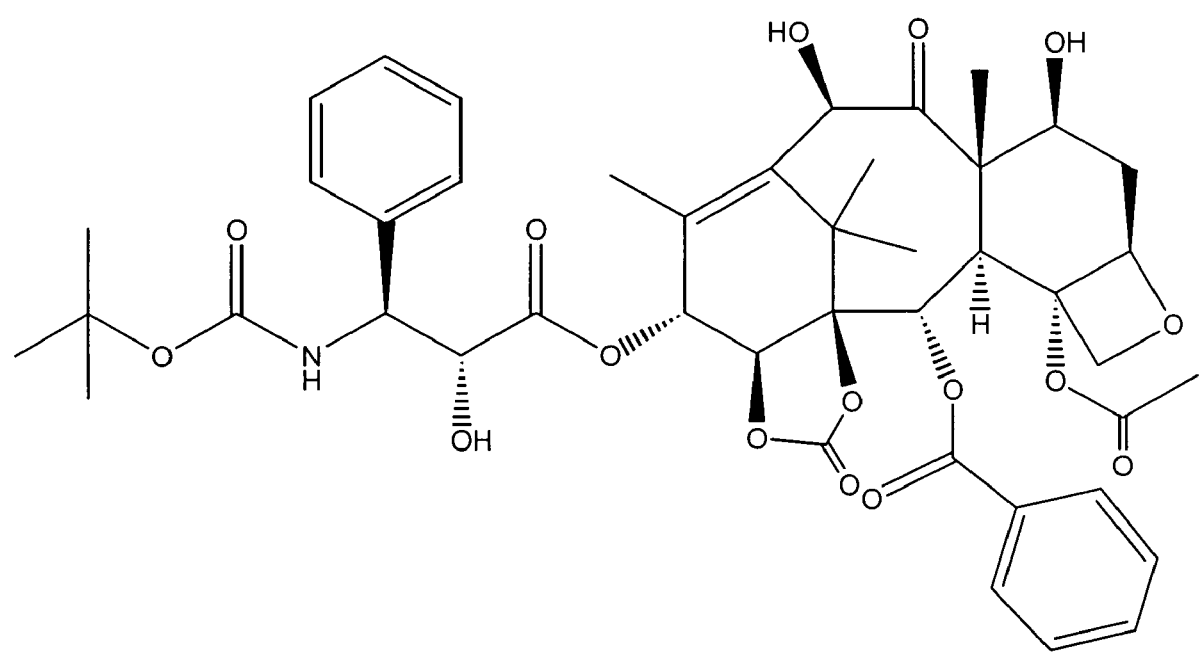
Figure 20:
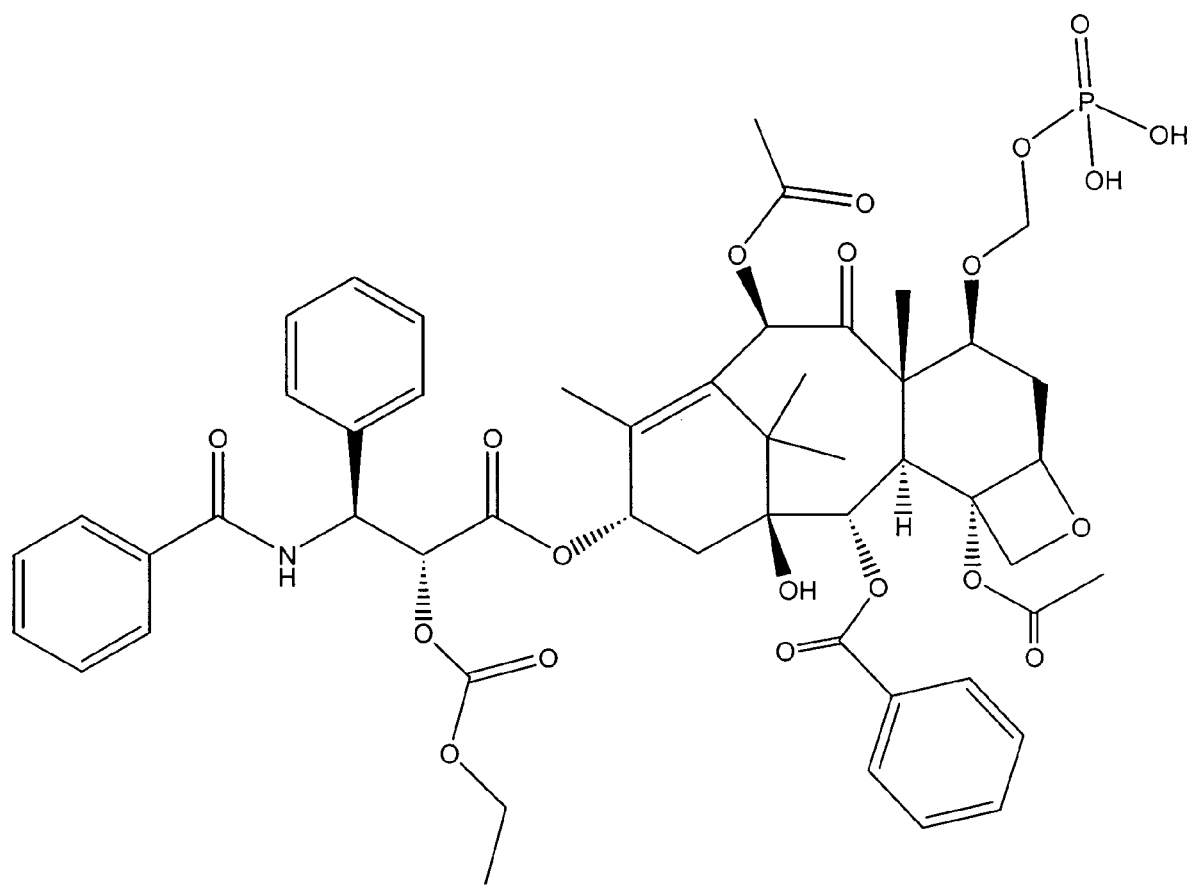
Figure 21:
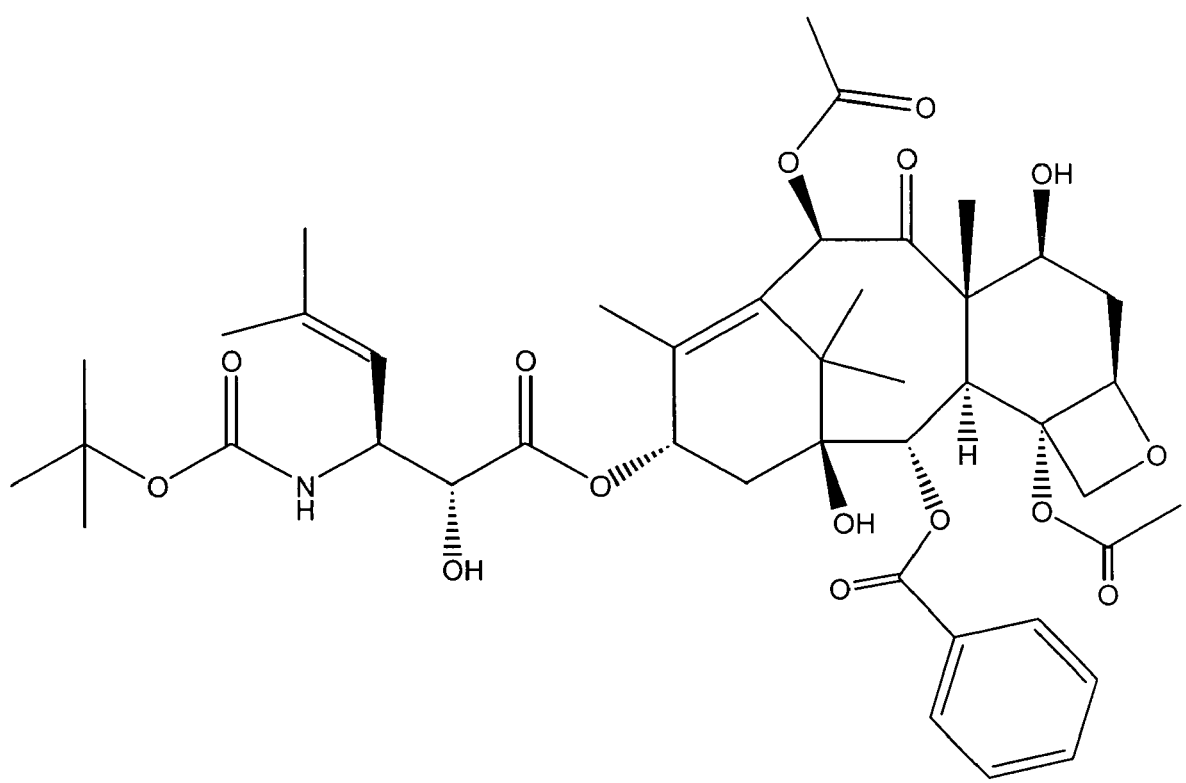
Figure 22:
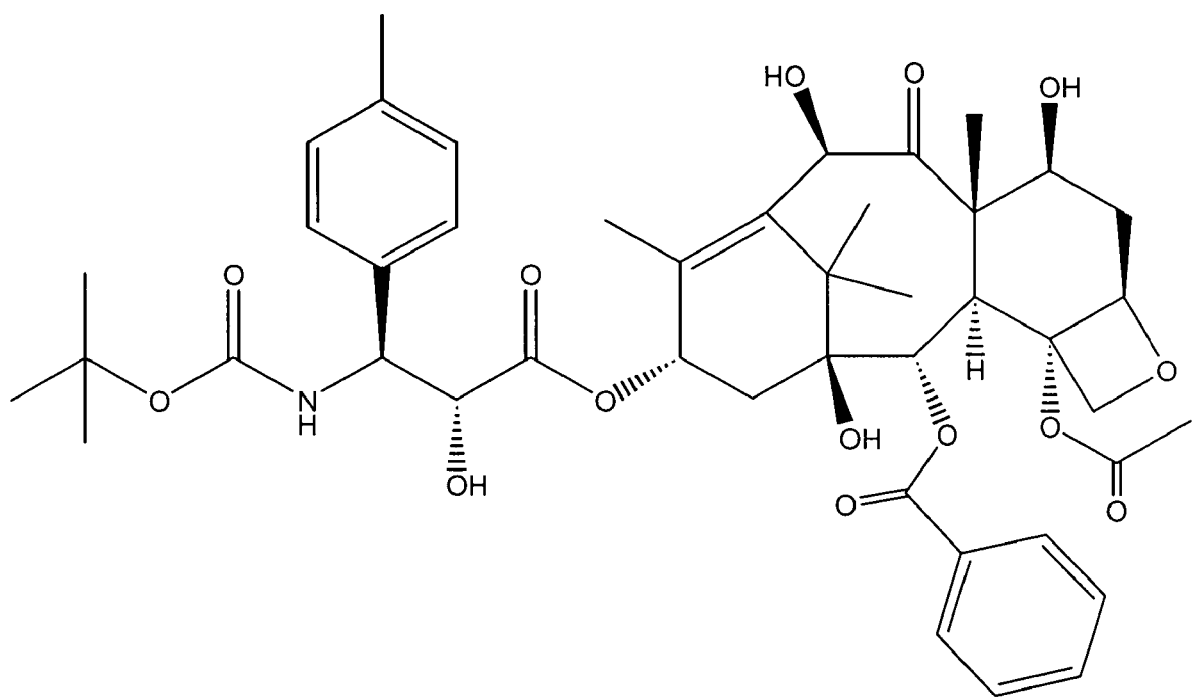
Figure 23:
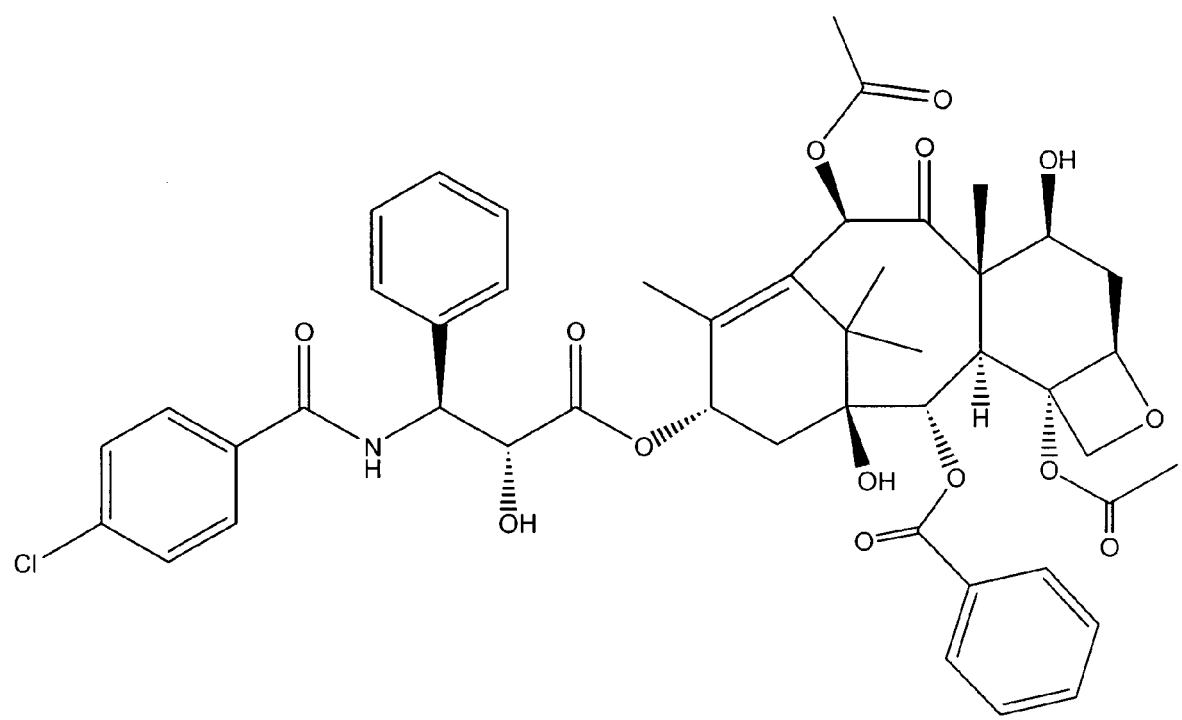

Paclitaxel, also referred to as "TAXOL", is a well-known anti-cancer drug which acts by enhancing and stabilizing microtubule formation. The structure of paclitaxel is shown in FIG. 1. Many analogs of paclitaxel are known, including Docetaxel, the structure of which is shown in FIG. 2. Docetaxel is also referred to as "TAXOTERE". The structures of other paclitaxel analogs are shown in FIGS. 3-23. These compounds have the basic taxane skeleton as a common structure feature and have also been shown to have the ability to arrest cells in the G2-M phases due to stabilization of microtubules. Thus, it is apparent from FIGS. 3-23 that a wide variety of substituents can decorate the taxane skeleton without adversely affecting biological activity. It is also apparent that zero, one or both of the cyclohexane rings of a paclitaxel analog can have a double bond at the indicated positions. For clarity purposes, the basic taxane skeleton is shown below in Structural Formula (VI):

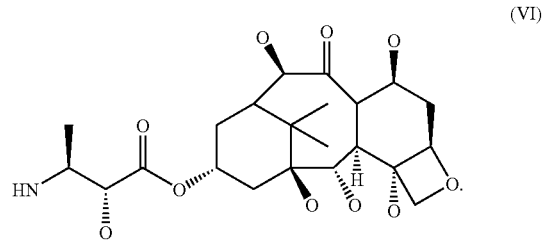

(VI)

Double bonds have been omitted from the cyclohexane rings in the taxane skeleton represented by Structural Formula (VI). The basic taxane skeleton can include zero or one double bond in one or both cyclohexane rings, as indicated in FIGS. 3-23 and Structural Formulas (VII) and (VIII) below. A number of atoms have also been omitted from Structural Formula (VI) to indicate sites in which structural variation commonly occurs among paclitaxel analogs. For example, substitution on the taxane skeleton with simply an oxygen atom indicates that hydroxyl, acyl, alkoxy or another oxygen-bearing substituent is commonly found at the site. These and other substitutions on the taxane skeleton can be made without losing the ability to enhance and stabilize microtubule formation. Thus, the term "paclitaxel analog" is defined herein to mean a compound which has the basic paclitaxel skeleton and which promotes microtubule formation. paclitaxel analogs may be formulated as a nanoparticle colloidal composition to improve the infusion time and to eliminate the need to deliver the drug with Cremophor which causes hypersensitivity reactions in some patients. An example of a paclitaxel analog formulated as a nanoparticle colloidal composition is ABI-007 which is a nanoparticle colloidal composition of protein-stabilized paclitaxel that is reconstituted in saline.

Typically, the paclitaxel analogs used herein are represented by Structural Formula (VII) or (VIII):

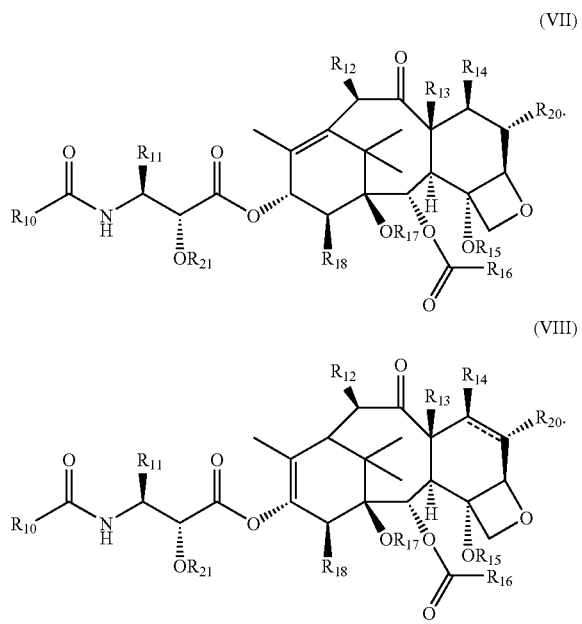

$R_{10}$ is a lower alkyl group, a substituted lower alkyl group, a phenyl group, a substituted phenyl group, —$SR_{19}$, —$NHR_{19}$ or —$OR_{19}$.

$R_{11}$ is a lower alkyl group, a substituted lower alkyl group, an aryl group or a substituted aryl group.

$R_{12}$ is —H, —OH, lower alkyl, substituted lower alkyl, lower alkoxy, substituted lower alkoxy, —O—C(O)-(lower alkyl), —O—C(O)-(substituted lower alkyl), —O—CH$_2$—O-(lower alkyl) —S—CH$_2$—O-(lower alkyl).

$R_{13}$ is —H, —CH$_3$, or, taken together with $R_{14}$, —CH$_2$—.

$R_{14}$ is —H, —OH, lower alkoxy, —O—C(O)-(lower alkyl), substituted lower alkoxy, —O—C(O)-(substituted lower alkyl), —O—CH$_2$—O—P(O)(OH)$_2$, —O—CH$_2$—O-(lower alkyl), —O—CH$_2$—S-(lower alkyl) or, taken together with $R_{20}$, a double bond.

$R_{15}$ —H, lower acyl, lower alkyl, substituted lower alkyl, alkoxymethyl, alkthiomethyl, —OC(O)—O(lower alkyl), —OC(O)—O(substituted lower alkyl), —OC(O)—NH(lower alkyl) or —OC(O)—NH(substituted lower alkyl).

$R_{16}$ is phenyl or substituted phenyl.

$R_{17}$ is —H, lower acyl, substituted lower acyl, lower alkyl, substituted, lower alkyl, (lower alkoxy)methyl or (lower alkyl)thiomethyl.

$R_{18}$ —H, —CH$_3$ or, taken together with $R_{17}$ and the carbon atoms to which $R_{17}$ and $R_{18}$ are bonded, a five or six membered a non-aromatic heterocyclic ring.

$R_{19}$ is a lower alkyl group, a substituted lower alkyl group, a phenyl group, a substituted phenyl group.

$R_{20}$ is —H or a halogen.

$R_{21}$ is —H, lower alkyl, substituted lower alkyl, lower acyl or substituted lower acyl.

Preferably, the variables in Structural Formulas (VII) and (VIII) are defined as follows: $R_{10}$ is phenyl, tert-butoxy, —S—CH$_2$—CH—(CH$_3$)$_2$, —S—CH(CH$_3$)$_3$, —S—(CH$_2$)$_3$CH$_3$, —O—CH(CH$_3$)$_3$, —NH—CH(CH$_3$)$_3$, —CH=C(CH$_3$)$_2$ or para-chlorophenyl; $R_{11}$ is phenyl, (CH$_3$)$_2$CHCH$_2$—, -2-furanyl, cyclopropyl or para-toluyl; $R_{12}$ is —H, —OH, CH$_3$CO— or —(CH$_2$)$_2$—N-morpholino; $R_{13}$ is methyl, or, $R_{13}$ and $R_{14}$, taken together, are —CH$_2$—;

$R_{14}$ is —H, —CH$_2$SCH$_3$ or —CH$_2$—O—P(O)(OH)$_2$; $R_{15}$ is CH$_3$CO—;

$R_{16}$ is phenyl; $R_{17}$ —H, or, $R_{17}$ and $R_{18}$, taken together, are —O—CO—O—;

$R_{18}$ is —H; $R_{20}$ is —H or —F; and $R_2$, is —H, —C(O)—CHBr—(CH$_2$)$_{13}$—CH$_3$ or —C(O)—(CH$_2$)$_{14}$—CH$_3$; —C(O)—CH$_2$—CH(OH)—COOH, —C(O)—CH$_2$—O—C(O)—CH$_2$CH(NH$_2$)—CONH$_2$, —C(O)—CH$_2$—O—CH$_2$CH$_2$OCH$_3$ or —C(O)—O—C(O)—CH$_2$CH$_3$.

Figure 24:
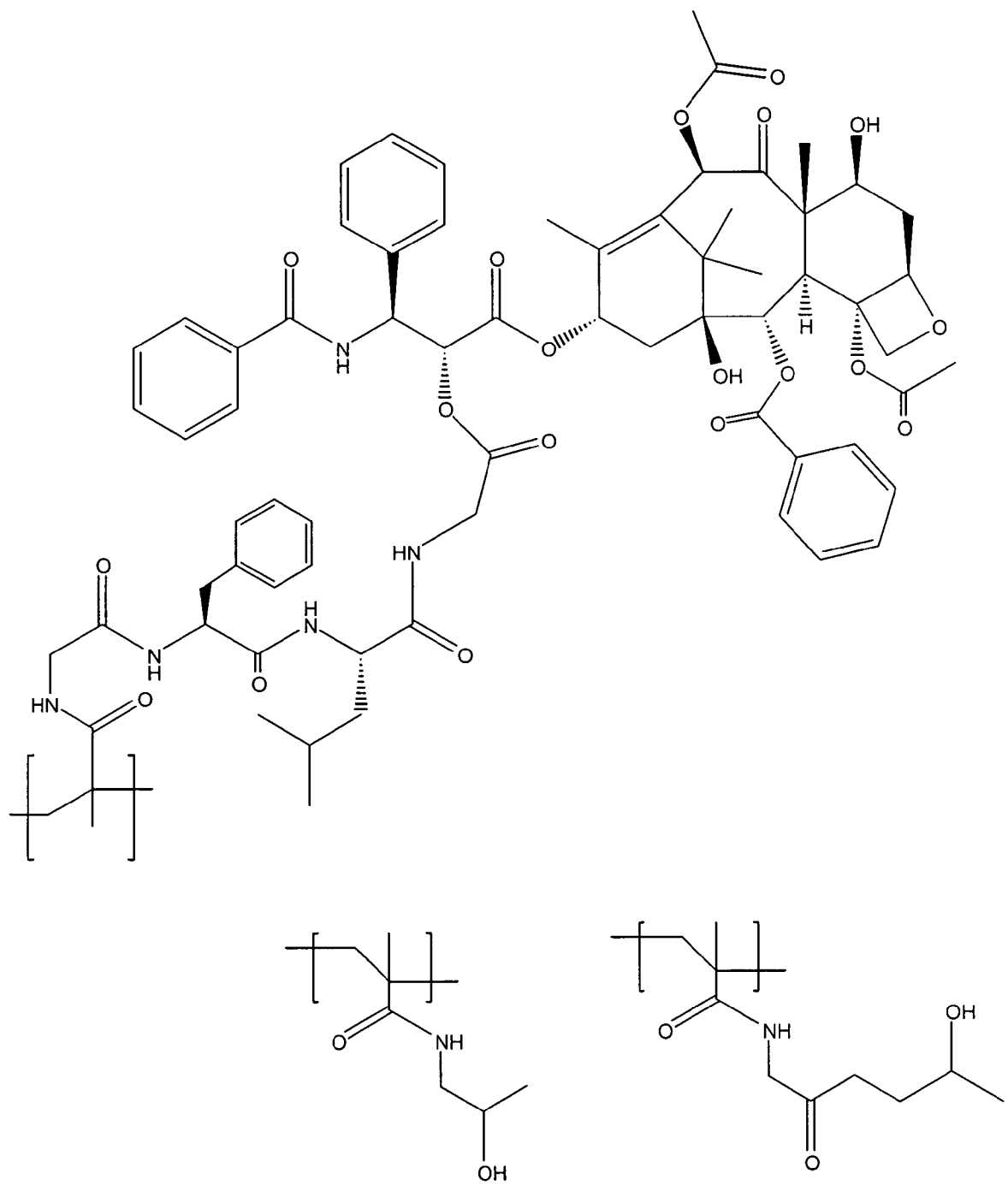
FIG. 24 is the structure of a polymer comprising a paclitaxel analog group pendent from the polymer backbone. The polymer is a terpolymer of the three monomer units shown.

A paclitaxel analog can also be bonded to or be pendent from a pharmaceutically acceptable polymer, such as a polyacrylamide. One example of a polymer of this type is shown in FIG. 24. The term "paclitaxel analog", as it is used herein, includes such polymers.

The bis(thio-hydrazide amide) disalts disclosed herein can be prepared by a method of the invention. The method of preparing the disclosed bis(thio-hydrazide amide) disalts includes the steps of combining a neutral bis(thio-hydrazide amide), an organic solvent and a base to form a bis(thio-hydrazide amide) solution; and combining the solution and an organic antisolvent, thereby precipitating a disalt of the bis(thio-hydrazide amide) (e.g., compounds represented by Structural Formulas (I)-(V)). The neutral forms of the disclosed bis(thio-hydrazide amide) disalts can be prepared according to methods described in U.S. Publication Nos. 2003/0045518 and 2003/0119914, both entitled SYNTHESIS OF TAXOL ENHANCERS and also according to methods described in U.S. Publication No. 2004/0225016 A1, entitled TREATMENT FOR CANCERS. The entire teachings of these publications are incorporated herein by reference.

Typically, at least about two molar equivalents of the base are employed for each molar equivalent of neutral bis(thio-hydrazide amide); more typically, from about 2 to about 5 equivalents, or preferably from about 2.0 to about 2.5 equivalents.

Suitable bases can be strong enough to react with a bis(thio-hydrazide amide) to produced a disalt. In various embodiments, the base can be an amine (e.g., triethylamine, diphenylamine, butylamine, or the like); an ammonium hydroxide (e.g., tetramethyammonium hydroxide, tetrabutylammonium hydroxide, or the like); an alkali metal hydroxide (lithium hydroxide, sodium hydroxide, potassium hydroxide, or the like) an alkali metal C1-C6 alkoxide, or an alkali metal amide (e.g., sodium amide, lithium diisopropyl amide, or the like). In some embodiments, the base is sodium hydroxide, potassium hydroxide, sodium C1-C6 alkoxide, potassium C1-C6 alkoxide, sodium amide, or potassium amide, or preferably, sodium hydroxide, sodium methoxide, or sodium ethoxide.

In various embodiments, the base can be an alkali metal hydride (e.g., sodium hydride, potassium hydride, or the like), a divalent metal base (e.g., magnesium oxide) a C1-C6 alkyl alkali metal (e.g., butyllithium), or an aryl alkali metal (e.g., phenyllithium). More typically, the base is lithium hydride, sodium hydride, potassium hydride, butyllithium, butylsodium, butylpotassium, phenyllithium, phenylsodium, or phenylpotassium.

As used herein, an alkali metal includes lithium, sodium, potassium, cesium and rubidium.

The organic solvent can be any organic solvent which is stable when the base is added to a mixture of the bis(thio-hydrazide amide) and the organic solvent. Typically, the organic solvent is polar enough to dissolve the bis(thio-hydrazide amide) salt formed by the method to form a solution. In various embodiments, the organic solvent is water-miscible. The organic solvent can generally be selected from a C1-C4 aliphatic alcohol (e.g., methanol, ethanol, 1-propanol, 2-propanol, or the like), a C1-C4 aliphatic ketone (e.g., acetone, methyl ethyl ketone, 2-butanone, or the like), a C2-C4 aliphatic ether (e.g., diethyl ether, dipropyl ether, diisopropyl ether, or the like), a C2-C4 cycloaliphatic ether (e.g., tetrahydrofuran, dioxane, or the like), dimethyl formamide, dimethyl sulfoxide, N-methyl pyrrolidone, a glycol (e.g., ethylene glycol, propylene glycol, tetramethylene glycol, or the like), an alkyl glycol ether (e.g., ethylene glycol dimethyl ether, or the like), and acetonitrile. More typically, the organic solvent can be selected from methanol, ethanol, propanol (e.g., 1-propanol, 2-propanol), butanol (e.g., 1-butanol, tert-butyl alcohol, or the like), acetone, tetrahydrofuran, and methyl ethyl ketone. Preferably, the organic solvent can be selected from methanol, ethanol, acetone, and methyl ethyl ketone.

As used herein, the organic antisolvent is a solvent that when added to the solution created by combining the base, the bis(thio-hydrazide amide) and the organic solvent, causes the bis(thiohydrazide amide) disalt to precipitate out of solution. Typically, the organic antisolvent can be selected from a C5-C10 alkane (e.g., pentane, petroleum ether, hexane, heptane, octane, isooctane, or the like), C5-C10 cycloalkane (e.g., cyclohexane, cyclopentane, or the like), a C3-C10 alkyl ester (e.g., ethyl acetate, propyl acetate, methyl butyrate, or the like, a C3-C10 alkyl ether (e.g., methyl ethyl ether, diethyl ether, methyl propyl ether, or the like), benzene, toluene, and xylene. More typically, the organic antisolvent can be selected from diethyl ether, dipropyl ether (e.g., propyl as 1-propyl or 2-propyl), methyl propyl ether, ethyl propyl ether, methyl tert-butyl ether, methyl acetate, ethyl acetate, propyl acetate, pentane, hexane, cyclohexane, heptane, and petroleum ether. In some embodiments, the organic antisolvent can be a C5-C10 alkane or C5-C10 cycloalkane. In various preferred embodiments, the organic antisolvent can be heptane; or, the organic antisolvent can be diethyl ether or ethyl acetate. In various preferred embodiments, the organic antisolvent can be methyl tert-butyl ether.

In various embodiments, the neutral bis(thio-hydrazide amide) can be substantially insoluble in the organic solvent, thereby forming a mixture, whereby combining the base with the mixture forms a bis(thio-hydrazide amide) solution. Typically, the bis(thio-hydrazide amide) solution can be clear. Generally, between about 0.25 and about 2.5 moles of the neutral bis(thio-hydrazide amide) are combined per each liter of organic solvent, or typically between about 0.75 and about 1.5 moles of the neutral bis(thio-hydrazide amide) are combined per each liter of organic solvent. Preferably, about 1 mole of the neutral bis(thio-hydrazide amide) are combined per each liter of organic solvent.

As used herein, a "bis(thio-hydrazide amide) solution," when formed from the organic solvent, the neutral bis(thio-hydrazide amide), and the base, can include one or more species such as the neutral bis(thio-hydrazide amide), the bis(thio-hydrazide amide) monosalt, the bis(thio-hydrazide amide) disalt, or the like.

In preferred embodiments, the organic solvent is ethanol. Preferably, the base is about 2 molar to about 5 molar aqueous sodium hydroxide, or more preferably from about 2 to about 2.5 molar.

In preferred embodiments, the organic solvent is acetone. Preferably, the base is about 2 molar to about 5 molar ethanolic sodium ethoxide, or more preferably from about 2 to about 2.5 molar.

The bis(thio-hydrazide amide) disalts prepared by the present invention are the disalts disclosed herein, including those represented by Structural Formulas (I)-(V). The neutral bis(thio-hydrazide amides) employed in the disclosed method to prepare the disalts represented by Structural Formulas (I)-(II) can be represented by the following Structural Formulas (I')-(II'), where the variables have the same values and preferred values as in Structural Formulas (I)-(II), respectively:

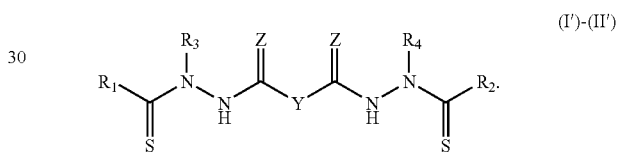

(I')-(II')

Thus, as used herein, a neutral bis(thio-hydrazide amide) has at least two hydrogens (e.g., the hydrogens bonded to the nitrogen atoms in Structural Formulas (I') and (II') which can react with the bases described herein to form a disalt.

In Structural Formula (I), $M^+$ is a pharmaceutically acceptable monovalent cation. $M^{2+}$ is a pharmaceutically acceptable divalent cation as described above.

In various preferred embodiments, the organic solvent can be acetone; the base can be ethanolic sodium ethoxide; the organic solvent can be ethanol; the base can be aqueous sodium hydroxide; the antisolvent can be heptane; the neutral bis(thio-hydrazide amide) can be:

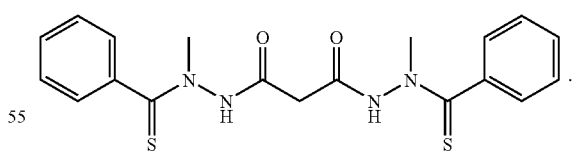

and/or the neutral bis(thio-hydrazide amide) can be:

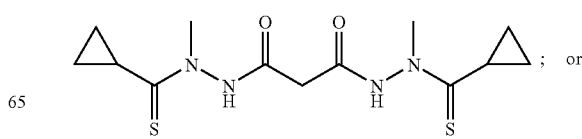

; or

-continued

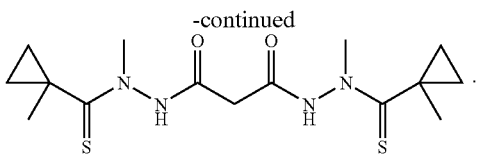

The present invention is illustrated by the following examples, which are not intended to be limiting in any way.

EXEMPLIFICATION

Example 1

Sodium; 2-(N'-methyl-N'-thiobenzoyl-hydrazinocarbonyl)-1-(methyl-thiobenzoyl-hydrazono)-ethanolate: Compound (3)

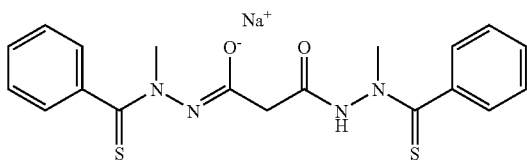

To a stirred clear solution of N-Malonyl-bis(N'-thiobenzoyl-N'-methyl hydrazide) (2 g) in THF (25 mL) was added sodium amide (0.2 g). The resultant mixture was stirred at room temperature for 4 hours. The precipitated product was collected by filtration and washed with THF and ether. The resulting solids were dried in vacuo (0.1 mmHg) for 12 hours. A light yellow solid weighing 1.53 g was obtained.

$^1$H-NMR (DMSO-$d_6$) δ (ppm): 2.2-2.7 (m, 2H), 3.1-3.7 (m, 6H), 7.1-7.5 (m, 10 H). Elem. Anal. Calcd. For $C_{19}H_{19}N_4NaO_2S_2 \cdot 0.55H_2O$: C 52.75%, H 4.66%, N12.98%; found: C 52.42%, H 4.41%, N 13.07%.

Example 2

Disodium: 2-(N'-methyl-N'-thiobenzoyl-hydrazinocarbonyl)-1-(methyl-thiobenzoyl-hydrazono)-ethanolate: Compound (1)

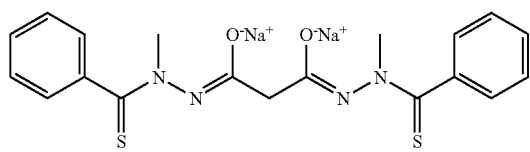

Method A: To a stirred clear solution of NaOH (0.358 g, 8.95 mmol) in $H_2O$ (10 mL) was added N-Malonyl-bis(N'-thiobenzoyl-N'-methyl hydrazide) (1.79 g, 4.48 mmol) at room temperature. The resultant solution was filtered, then the filtrate was cooled with a dry-ice/$^i$PrOH bath followed by freeze-drying to obtain Compound 1 as a solid.

$^1$H-NMR (DMSO-$d_6$) δ (ppm): 2.15 (s, 2H), 3.45 (s, 6H), 7.0-7.2 (m, 6 H), 7.2-7.4 (m, 4H). Elem. Anal. Calcd for $C_{19}H_{18}N_4Na_2O_2S_2 \cdot 0.7H_2O$ (457.22): C 49.91; H 4.29; N12.26; found: C 49.95; H 4.17; N12.05.

Method B: To a stirred solution of N-Malonyl-bis(N'-thiobenzoyl-N'-methyl hydrazide) (0.92 g) in THF (15 mL) was added a solution of NaOH (0.184 g) in MeOH (15 mL). After 15 min stirring at room temperature, the resultant solution was concentrated and precipitated with ether to yield 1 g of a light orange powder after filtration. The physical data for the precipitate was is in accordance with that obtained from Method A.

Example 3

Lithium; 2-(N'-methyl-N'-thiobenzoyl-hydrazinocarbonyl)-1-(methyl-thiobenzoyl-hydrazono)-ethanolate: Compound (4)

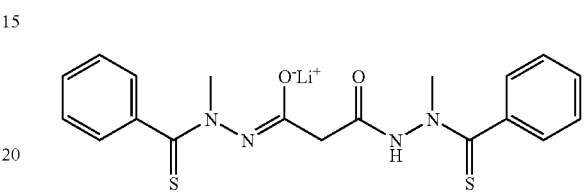

To a solution of N-Malonyl-bis(N'-thiobenzoyl-N'-methyl hydrazide) (8 g, 20 mmol) in THF (90 ml) was added llithium diisopropylamide (LDA) (20 mmol, 2M in heptane/THF/ethylbenzene) at 0° C., and the mixture was stirred for 2 hours. The precipitate was collected, washed with EtOAc, and dried to give a mono lithium salt of N-Malonyl-bis(N'-thiobenzoyl-N'-methyl hydrazide) (6.5 g).

$^1$H-NMR (DMSO-$d_6$) δ (ppm), 7.71-7.32 (m, 10H), 3.72-2.73(m, 9H).

Example 4

Dilithium; 2-(N'-methyl-N'-thiobenzoyl-hydrazinocarbonyl)-1-(methyl-thiobenzoyl-hydrazono)-ethanolate: Compound (5)

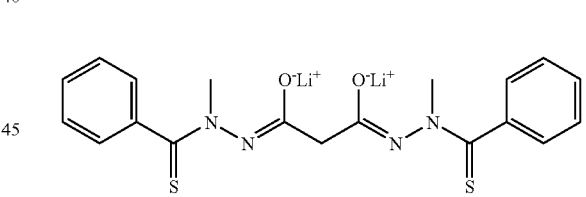

Compound 5 was prepared according to the method described in Example 3 except that 2 equivalents of LDA were used instead of one equivalent.

$^1$H-NMR (DMSO-$d_6$) δ (ppm): 7.61-7.12 (m, 10H), 3.82-2.29(m, 8H).

Example 5

Ethanolamine; 2-(N'-methyl-N'-thiobenzoyl-hydrazinocarbonyl)-1-(methyl-thiobenzoyl-hydrazono)-ethanolate: Compound (6)

The monoethanolamine compound was made in a similar to that in Example 3 by using one equivalent of ethanolamine instead of LDA.

$^1$H-NMR 4783 (DMSO-$d_6$) δ (ppm): 7.72-7.33 (m, 10H), 3.80-2.63(m, 13H).

Example 6

Diethanolamine; 2-(N'-methyl-N'-thiobenzoyl-hydrazinocarbonyl)-1-(methyl-thiobenzoyl-hydrazono)-ethanolate: Compound (7)

The diethanolamine compound was made in a similar to that in Example 3 by using two equivalents of ethanolamine instead of one equivalent of LDA.

$^1$H-NMR 4783 (DMSO-$d_6$) δ (ppm): 7.69-7.31 (m, 10H), 3.78-2.64(m, 16H)

Example 7

Magnesium; 2-(N'-methyl-N'-thiobenzoyl-hydrazinocarbonyl)-1-(methyl-thiobenzoyl-hydrazono)-ethanolate: Compound (8)

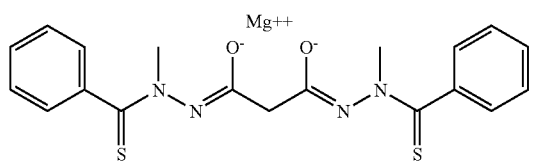

The pH of a suspension of MgO (440 mg, 1.1 mmol, 15 mL) in water was adjusted to 2-3 to form a clear solution. To this solution was added dilithium; 2-(N'-methyl-N'-thiobenzoyl-hydrazinocarbonyl)-1-(methyl-thiobenzoyl-hydrazono)-ethanolate (1 mmol), and the mixture was stirred for 3 hours. The precipitate that formed was collected and washed with water, and then dried to give the magnesium salt (2.1 g).

$^1$H-NMR (DMSO-$d_6$) δ (ppm): 7.68-7.32 (m, 10H), 3.98-2.49(m, 8H).

Example 8

Calcium; 2-(N'-methyl-N'-thiobenzoyl-hydrazinocarbonyl)-1-(methyl-thiobenzoyl-hydrazono)-ethanolate: Compound (9)

The calcium compound was made in a similar to that in Example 7 by using Ca(OH)$_2$ instead of MgO.

$^1$H-NMR (DMSO-$d_6$) δ (ppm): 7.67-7.34 (m, 10H), 3.91-2.55(m, 8H).

Example 9

Monopotassium; 2-(N'-methyl-N'-thiobenzoyl-hydrazinocarbonyl)-1-(methyl-thiobenzoyl-hydrazono)-ethanolate: Compound (10)

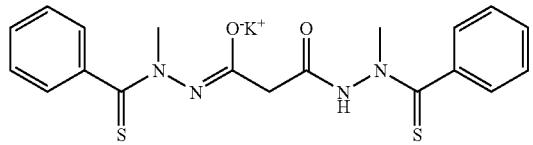

N-Malonyl-bis(N'-thiobenzoyl-N'-methyl hydrazide) (micronized), 5.006 g (12.5 mmol) was suspended in 70 mL of absolute ethanol. Into this suspension was added with stirring 12.4 mL (1 equivalent) of a 1.008 N solution of potassium hydroxide in methanol. The resulting solution was filtered through a glass acrodisc (Gelman) and concentrated to about 5 mL. Into this concentrated solution, 5 mL of ethyl acetate was added, followed by anhydrous ether until the resulting solution turned cloudy. This solution was left for crystallization overnight. A hardened precipitate was broken up with a spatula, filtered out, washed twice with anhydrous ether and vacuum-dried at 50° C. to afford a mono-potassium salt as pale-yellow solids (4.05 g, 70%).

$^1$H NMR (DMSO-$d_6$) (a mixture of tautomers): δ (ppm): 7.4-7.25, 7.22 (m, 10H), 3.60, 3.45 and 3.19 (singlets, 6H), 2.78, 2.39 and 1.96 (singlets, 3H) ). IR (KBr): 1686s, 1572, 1478 cm$^{-1}$. Anal. Calcd for $C_{19}H_{19}K_2N_4O_2S_2+H_2O$: C, 49.98; H, 4.64; K, 8.56; N, 12.27. Found: C, 49.99; H, 4.51; K, 8.67; N, 11.91.

Example 10

Dipotassium; 2-(N'-methyl-N'-thiobenzoyl-hydrazinocarbonyl)-1-(methyl-thiobenzoyl-hydrazono)-ethanolate: Compound (2)

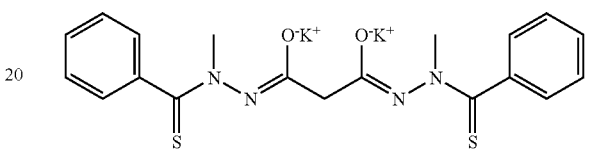

Method A: N-Malonyl-bis(N'-thiobenzoyl-N'-methyl hydrazide) (micronized, 5.006 g, 12.5 mmol) was treated with 24.95 mL (2 equivalent) of 1.002 N solution of potassium hydroxide in water (volumetric standard solution, Aldrich). All material except a few particles dissolved, and 6 mL of Milli-Q water was added to afford a solution with some tiny particles remaining. The solution was then filtered through a glass acrodisc (Gelman), the filter was rinsed with 2 mL of Milli-Q water, and the combined solution was diluted to 50 mL with Milli-Q water and lyophilized to produce a title compound as yellow foams (6.17 g).

$^1$H NMR (DMSO-$d_6$): δ (ppm): 7.34-7.31 (m, 4H), 7.11-7.09 (m, 6H), 3.51 (m, 6H), 2.11 (s, 2H). IR (KBr): 1561, cm$^{-1}$. Anal. Calcd for $C_{19}H_{18}K_2N_4O_2S_2+H_2O$; C, 46.13; H, 4.07; K, 15.81; N, 11.33. Found: C, 46.08; H, 4.21; K, 16.05; N, 11.32.

Method B: Alternatively, N-Malonyl-bis(N'-thiobenzoyl-N'-methyl hydrazide) (micronized, 5.006 g, 12.5 mmol) was dissolved in anhydrous THF (62 mL). Into this solution, and 25.1 mL (2 equivalent) of 1.008N solution of potassium hydroxide in methanol (volumetric standard solution, Aldrich) was added. From the resulting solution, solvent was removed under reduced pressure to leave about 5 mL of an oily residue, which was triturated with anhydrous ether until a pale yellow solid was obtained. The solid was filtered out, washed twice with anhydrous ether and vacuum-dried at 50° C., to yield the dipotassium salt as a powder (4.3 g, 73%). NMR data were identical with those obtained above in Method A.

Example 11

Cholin; 2-(N'-methyl-N'-thiobenzoyl-hydrazinocarbonyl)-1-(methyl-thiobenzoyl-hydrazono)-ethanolate: Compound (11)

Into a stirred solution of N-Malonyl-bis(N'-thiobenzoyl-N'-methyl hydrazide) (2 g, 5 mmol) in 65 mL of anhydrous THF was added dropwise 1.32 mL of a solution of choline hydroxide (45% solution in MeOH) in 10 ml of anhydrous THF. At first, a clear solution was formed, followed by precipitation of a fine solid. The solution was left for 1 hour for the precipitation to be completed. The precipitate was filtered out, washed twice with ether:THF (2:1, v/v), then once with anhydrous ether, and vacuum-dried at 50° C. to obtain the titled salt as a pale yellow powder (2.14 g, 85%).

$^1$H NMR (DMSO-d$_6$) (a mixture of tautomers): δ (ppm): 7.4-7.35, 7.24-7.19 (m, 10H), 3.83-3.80 (m, 2H), 3.40-3.37 (m, 2H), 3.60, 3.45 and 3.19 (singlets, 6H), 3.10 (m, 9H), 2.64, 2.32 and 2.06 (singlets, 3H)). IR (KBr): 1686s, 1586s, 1482s cm$^{-1}$.

Example 12

Disodium 2-(N'-methyl-N'-thio-1-methylcyclopropyl-hydrazinocarbonyl)-1-(methyl-thio-1-methylcyclopropyl-hydrazono)-ethanolate: Compound (12)

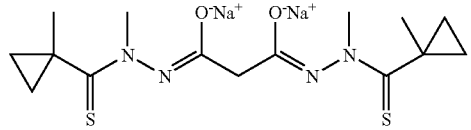

Into a stirred clear solution of NaOH (24.7 mg, 0.62 mmol) in H$_2$O (5 mL) was added N-Malonyl-bis(N'-thio-1-methyl-cyclopropyl-N'-methyl hydrazide) (110 mg, 0.31 mmol) at room temperature. The resultant solution was filtered, then the filtrate was cooled with a dry-ice/$^i$PrOH bath followed by freeze-drying to obtain Compound (12) as a solid.

$^1$H-NMR (DMSO-d$_6$) δ (ppm): 0.38 (t, 4H, J=5), 0.83 (t, 4H, J=5), 1.18 (s, 6 H), 2.62 (s, 2H), 3.38 (s, 6H).

Example 13

Disodium; 2-(N'-methyl-N'-thiocyclopropyl-hydrazinocarbonyl)-1-(methyl-thiocyclopropyl-hydrazono)-ethanolate: Compound (13)

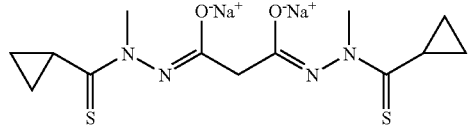

The disodium compound was prepared by a similar method to that used for Example 12.

$^1$H-NMR (DMSO-d$_6$) δ (ppm): 0.45 (m, 4H), 0.85 (m, 4H), 2.61 (s, 2 H), 2.70 (m, 1H), 3.41 (s, 6H).

Example 14

Dipotassium: 2-(N'-methyl-N'-thio-1-methylcyclopropyl-hydrazinocarbonyl)-1-(methyl-thio-1-methylcyclopropyl-hydrazono)-ethanolate: Compound (14)

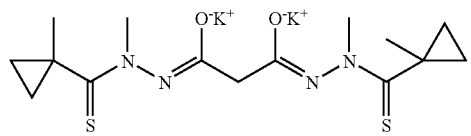

The dipotassium compound was prepared by a method similar to that used for Example 12 except that KOH was used instead of NaOH.

$^1$H-NMR (DMSO-d$_6$) δ (ppm): 0.39 (m, 4H), 0.82 (m, 4H), 1.18 (s, 6 H), 2.60 (s, 2H), 3.38 (s, 6H).

Example 15

Bis (Thio-Hydrazide Amide) Disalts Have Significantly Greater Solubility Than The Corresponding Monosalts And Neutral Forms A compound was weighed and water was added to the compound such that the resulting concentration of the compound was about 100 mg/mL. The mixture was then shaken well and sonicated (about 5-10 min at about 50° C.). If the added amounts of the compound were totally solubilized, more amounts of the compound were added to the solution and the mixture was shaken well and sonicated until a suspension was achieved. The suspension was then filtered through a 0.2 μm filter. The filtered solution was diluted with DMSO. Then the mixture was analyzed by HPLC to determine the concentration of the compound.

The HPLC system consisted of the HP 1100 Model (Agilent, Wilmington, Del.) equipped with a model 1100 quaternary pump, a model 1100 autosampler, a model 1100 Diode-Array Detector for UV detection at 280 nm. HPLC analysis was performed using a gradient mobile phase consisting of acetonitrile-water containing 0.1% formic acid. Mobile phases were degassed and filtered through a solvent filtration apparatus and pumped at a constant rate of 1.0 mL/min. Separation was made on an XTerra MS C18 analytical column, 4.6 mm i.d.×150 mm, (Waters Corp., Milford, Mass., USA) fitted with a pre-column filter (XTerra MS C18, 3.9 mm×20 mm). The column was maintained at 40° C. Data acquisition and instrument setting were controlled using HP Chemstation software (version 8.03).

Solubility data for each compound tested are shown below in Table 1.

TABLE 1

| | | Solubility Data | |
|---|---|---|---|
| Samples | Salts | Compound | Solubility in water (mg/mL) |
| A | — | Neutral Form of Compound 1 | <0.1 |
| B | 2Na$^+$ | 1 | >1000 |
| C | Li$^+$ | 4 | 53.5 |
| D | 2Li$^+$ | 5 | 626.0 (>500) |
| E | Na$^+$ | 3 | 52.8 |
| F | 2K$^+$ | 2 | >1000 |
| G | K$^+$ | 10 | 41.2 |
| H | Ca$^{2+}$ | 9 | 18.9 |
| I | HEA$^+$ | 6 | 51.5 |
| J | 2HEA$^+$ | 7 | 231.1 (>200) |
| K | Mg$^{2+}$ | 8 | 43.5 |
| L | Choline$^+$ | 11 | 264.0 (>200) |
| M | 2Na$^+$ | 12 | >1000 |
| N | 2Na$^+$ | 13 | >1000 |
| O | 2K$^+$ | 14 | >1000 |

As can be seen in Table 1, the bis(thio-hydrazide amide) disalts, for example, Compounds 1, 2, 5, 7, 12, 13 and 14, have significantly greater water solubility than the corresponding neutral or monosalt compounds. In particular, Compounds 1 and 2 showed significantly greater water solubility than the corresponding neutral form. Similarly, disalts compounds, Compounds 1, 2, 5 and 7, showed much greater water solubility than the corresponding monosalt compounds, Compounds 3, 4, 6 and 10.

Example 16

Bis (Thio-Hydrazide Amide) Disalts Have Significantly Greater Bioavailability Than The Corresponding Monosalts And Neutral Forms A) Procedure for Pharmacokinetics Study in Dog Male beagle dogs were acclimated for at least one week prior to use, were fed laboratory chow and water ad libitum, and were housed in temperature and humidity controlled rooms. Compounds were prepared as a solution for intravenous injection or a capsule for oral administration. Three dogs were used for the study. Compounds were injected intravenously via cephalic vein or by oral gavage. The dose was adjusted based on the animal's body weight. Blood samples were collected at intervals of 5, 10 and 30 min and 1, 2, 4, 6, 8 and 24 hr (example) after administration of the compound and plasma samples were prepared after centrifugation (5000 rpm, 8 min) of whole blood samples. Compound in plasma was measured by a liquid chromatography with tandem mass spectrophotometer (LC/MS/MS) after 50 µl of these samples were extracted by protein precipitation with acetonitrile. The compound concentration was determined by the standard curve (concentration vs. peak area) made with the same extraction procedure of controlled plasma. The area under curve (AUC) was calculated using the modified trapezoidal method. The portion of AUC from the last measurable plasma concentration to infinity was estimated by C/k, where k was expressed by the least square regression of the log-linear concentration time points and C represents the last measurable plasma concentration. Bioavailability was calculated by AUCpo/AUCiv.

B) Bioanalytical Method of Compounds (1) and (3) in Plasma by LC/MS/MS

Compounds (1) and (3) and its internal standard were extracted from heparinized plasma by protein precipitation with acetonitrile. Chromatography was achieved on an XTerra column (Waters, particle size: 5 µm; 100 mm×3.0 mm i.d.) using a mixture of acetonitrile, water and formic acid. Analysis was performed on a Sciex API 365 tandem mass spectrometer with turbo ion spray interface. Negative ions were measured using the multiple-reaction-monitoring (MRM) mode with m/z 399.0→165.1. The run time was 9 min per sample, and Compounds (1) and (3) were quantitated by a peak area ratio using $1/X^2$-weighted least-square linear regression plot.

Bioavailability data for each compound tested are shown below in Table 2.

TABLE 2

Bioavailability Data

| Samples | Salts | Compounds | Bioavailability (%) |
|---|---|---|---|
| 1 | — | Neutral Form of Compound (1) | 4.8 |
| 2 | $2Na^+$ | 1 | 80 |
| 3 | $Na^+$ | 3 | 35 |

As can be seen in Table 2, the disalt compound, Compound (1), showed much greater bioavailability than the corresponding neutral compound or monosalt compound, Compound (3).

Example 17

Process Method for Preparing Disodium Salts

I. General Method

About 50 mmol of the neutral form of a compound of the invention is suspended in 50 mL of acetone. About 2.04 equivalents of NaOH is dissolved in ethanol to form 38 mL of a 21% solution. The NaOH solution is added to the suspension of the compound while maintaining the temperature at about 0° C. The mixture is stirred for about 20 min. to give a clear solution, then about 1.2 mL of water is add. The solution is allowed to come to room temperature and about 400 mL of heptane is added. The solution is allowed to stir about 12 hours and the resulting precipitate is collected by filtration.

The precipitate is added to about 60 mL of acetone and stirred for 2 hours at room temperature, then collected by filtration and dried under vacuum for 1 hour at about 50° C. to yield the pure disodium salt of the compound.

II. Preparation of Disodium; 2-(N'-methyl-N'-thiobenzoyl-hydrazinocarbonyl)-1-(methyl-thiobenzoyl-hydrazono)-ethanolate: Compound (1)

Compound (1) was prepared by the above general method. The analytical data was as follows:

$^1$H NMR(DMSO-$d_6$) (ppm) 7.38-7.02 (m, 10H), 3.51 (s, 6H), 2.13 (s, 2H)

Elemental Analysis: Calculated for $C_{19}H_{20}N_4Na_2O_2S_2$: C 49.34, H 4.36, N 12.11, S 13.87; found C 49.28, H 4.18, N 11.91, S 13.63

Examples 18-20

Preparation of Disodium Bis(thio-hydrazide amide) Solution

A sample of a bis(thio-hydrazide amide) (Compound 1, 15 grams) was combined with 40 mL of absolute ethanol to form a mixture as a slurry. Aqueous sodium hydroxide (3.0 grams NaOH in 3.0 mL H20) was added to the mixture with stirring at room temperature, and the mixture was cooled to not exceed 35 degrees C. The aqueous sodium hydroxide addition vessel was rinsed with 1 mL of water and 5 mL of ethanol, and the rinses were added to the mixture. After addition, the mixture was stirred for 110 minutes. The resulting yellow disodium bis(thio-hydrazide amide) solution was separated into three equal portions for the following examples.

Example 18

63% Yield of Bis(thio-hydrazide amide) Disodium Salt

A one-third portion of the above yellow disodium bis(thio-hydrazide amide) solution was combined with 17 mL of methyl tert-butyl ether and stirred for 60 minutes (precipitation occurred in less than 30 minutes). The resulting slurry was filtered, washed with 10 mL of a 1:1 mixture of ethyl acetate:methyl tert-butyl ether, followed by 5 mL of ethyl acetate. Residual solvent was removed by vacuum to give 3.51 grams (63%) of the disodium salt of Compound (1) as a pale yellow solid. A yellow contaminant was visible.

Example 19

87% Yield of Pure Bis(thio-hydrazide amide) Disodium Salt

A one-third portion of the above yellow disodium bis(thio-hydrazide amide) solution was combined with 17 mL of methyl tert-butyl ether and stirred for 60 minutes (precipitation occurred in less than 30 minutes). An additional 17 mL of methyl tert-butyl ether was added to the resulting thick slurry, and was stirred for an additional 14 hours. The resulting slurry was filtered, washed with 10 mL of a 1:1 mixture of ethyl acetate:methyl tert-butyl ether, followed by 10 mL of ethyl acetate. Residual solvent was removed by vacuum to give 4.84 grams (87%) of the disodium salt of Compound (1) as a pale yellow solid. No yellow contaminant was visible.

Example 20

96% Yield of Pure Bis(thio-hydrazide amide) Disodium Salt

A one-third portion of the above yellow disodium bis(thio-hydrazide amide) solution was combined with 17 mL of methyl tert-butyl ether and stirred for 60 minutes (precipitation occurred in less than 30 minutes). An additional 34 mL of methyl tert-butyl ether was added to the resulting thick slurry, and was stirred for an additional 14 hours. The resulting slurry was filtered, washed with 10 mL of a 1:1 mixture of ethyl acetate:methyl tert-butyl ether, followed by 10 mL of ethyl acetate. Residual solvent was removed by vacuum to give 5.35 grams (96%) of the disodium salt of Compound (1) as a pale yellow solid. No yellow contaminant was visible.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by the following structural formula:

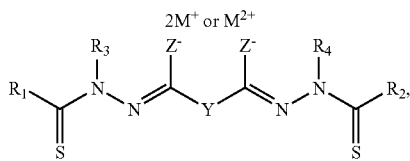

wherein:
Y is a covalent bond or a substituted or unsubstituted straight chained hydrocarbyl group;
$R_1$-$R_4$ are independently —H, an aliphatic group, a substituted aliphatic group, an aryl group or a substituted aryl group, or $R_1$ and $R_3$ taken together with the carbon and nitrogen atoms to which they are bonded, and/or $R_2$ and $R_4$ taken together with the carbon and nitrogen atoms to which they are bonded, form a non-aromatic heterocyclic ring optionally fused to an aromatic ring;
Z is —O or —S; and
$M^+$ is a pharmaceutically acceptable monovalent cation and $M^{2+}$ is a pharmaceutically acceptable divalent cation.

2. The compound of claim 1, wherein the compound is represented by the following structural formula:

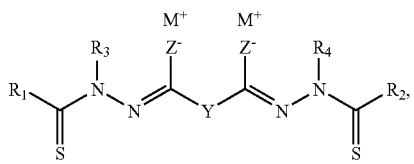

wherein $M^+$ is $Na^+$ or $K^{30}$.

3. The compound of claim 2, wherein Z is O; $R_1$ and $R_2$ are the same; and $R_3$ and $R_4$ are the same.

4. The compound of claim 3, wherein:
Y is a covalent bond, —C($R_5R_6$)—, —(CH$_2$CH$_2$)—, trans-(CH=CH)—, cis-(CH=CH)— or —(CC)— group; and $R_5$ and $R_6$ are each independently —H, an aliphatic or substituted aliphatic group, or $R_5$ is —H and $R_6$ is a substituted or unsubstituted aryl group, or $R_5$ and $R_6$, taken together, are a C2-C6 substituted or unsubstituted alkylene group.

5. The compound of claim 4, wherein:
Y is —C($R_5R_6$)—;
$R_1$ and $R_2$ are each a substituted or unsubstituted aryl group; and
$R_3$ and $R_4$ are each a substituted or unsubstituted aliphatic group.

6. The compound of claim 5, wherein $R_5$ is —H and $R_6$ is —H, an aliphatic or substituted aliphatic group; $R_3$ and $R_4$ are each an alkyl group; and $R_6$ is —H or methyl.

7. The compound of claim 6, wherein $R_1$ and $R_2$ are each a substituted or unsubstituted phenyl group and $R_3$ and $R_4$ are each methyl or ethyl.

8. The compound of claim 4, wherein
Y is —CR$_5$R$_6$—;
$R_1$ and $R_2$ are both a substituted or unsubstituted aliphatic group;
$R_5$ is —H; and
$R_6$ is —H or an optionally substituted aliphatic group.

9. The compound of claim 8, wherein $R_1$ and $R_2$ are both a C3-C8 cycloalkyl group optionally substituted with at least one alkyl group; $R_3$ and $R_4$ are both an alkyl group; and $R_6$ is —H or methyl.

10. The compound of claim 9, wherein $R_1$ and $R_2$ are both cyclopropyl or 1-methylcyclopropyl.

11. The compound of claim 1, wherein the compound is represented by the following structural formula:

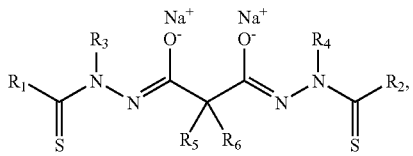

wherein:
$R_1$ and $R_2$ are both phenyl; $R_3$ and $R_4$ are both methyl; $R_5$ and $R_6$ are both —H;
$R_1$ and $R_2$ are both phenyl; $R_3$ and $R_4$ are both ethyl; $R_5$ and $R_6$ are both —H;
$R_1$ and $R_2$ are both 4-cyanophenyl; $R_3$ and $R_4$ are both methyl; $R_5$ is methyl; $R_6$ is —H;
$R_1$ and $R_2$ are both 4-methoxyphenyl; $R_3$ and $R_4$ are both methyl; $R_5$ and $R_6$ are both —H;
$R_1$ and $R_2$ are both phenyl; $R_3$ and $R_4$ are both methyl; $R_5$ is methyl; $R_6$ is —H;
$R_1$ and $R_2$ are both phenyl; $R_3$ and $R_4$ are both ethyl; $R_5$ is methyl; $R_6$ is —H;
$R_1$ and $R_2$ are both 4-cyanophenyl; $R_3$ and $R_4$ are both methyl; $R_5$ and $R_6$ are both —H;
$R_1$ and $R_2$ are both 2,5-dimethoxyphenyl; $R_3$ and $R_4$ are both methyl; $R_5$ and $R_6$ are both —H;
$R_1$ and $R_2$ are both 2,5-dimethoxyphenyl; $R_3$ and $R_4$ are both methyl; $R_5$ is methyl; $R_6$ is —H;
$R_1$ and $R_2$ are both 3-cyanophenyl; $R_3$ and $R_4$ are both methyl; $R_5$ and $R_6$ are both —H;
$R_1$ and $R_2$ are both 3-fluorophenyl; $R_3$ and $R_4$ are both methyl; $R_5$ and $R_6$ are both —H;
$R_1$ and $R_2$ are both 4-chlorophenyl; $R_3$ $R_4$ are both methyl; $R_5$ is methyl; $R_6$ is —H;

$R_1$ and $R_2$ are both 2-dimethoxyphenyl; $R_3$ and $R_4$ are both methyl; $R_5$ and $R_6$ are both —H;

$R_1$ and $R_2$ are both 3-methoxyphenyl; $R_3$ and $R_4$ are both methyl; $R_5$ and $R_6$ are both —H;

$R_1$ and $R_2$ are both 2,3-dimethoxyphenyl; $R_3$ and $R_4$ are both methyl; $R_5$ and $R_6$ are both —H;

$R_1$ and $R_2$ are both 2,3-dimethoxyphenyl; $R_3$ and $R_4$ are both methyl; $R_5$ is methyl; $R_6$ is —H;

$R_1$ and $R_2$ are both 2,5-difluorophenyl; $R_3$ and $R_4$ are both methyl; $R_5$ and $R_6$ are both —H;

$R_1$ and $R_2$ are both 2,5-difluorophenyl; $R_3$ and $R_4$ are both methyl; $R_5$ is methyl; $R_6$ is —H;

$R_1$ and $R_2$ are both 2,5-dichlorophenyl; $R_3$ and $R_4$ are both methyl; $R_5$ and $R_6$ are both —H;

$R_1$ and $R_2$ are both 2,5-dimethylphenyl; $R_3$ and $R_4$ are both methyl; $R_5$ and $R_6$ are both —H;

$R_1$ and $R_2$ are both 2,5-dimethoxyphenyl; $R_3$ and $R_4$ are both methyl; $R_5$ and $R_6$ are both —H;

$R_1$ and $R_2$ are both phenyl; $R_3$ and $R_4$ are both methyl; $R_5$ and $R_6$ are both —H; $R_1$ and $R_2$ are both 2,5-dimethoxyphenyl; $R_3$ and $R_4$ are both methyl; $R_5$ is methyl; $R_6$ is —H;

$R_1$ and $R_2$ are both cyclopropyl; $R_3$ and $R_4$ are both methyl; $R_5$ and $R_6$ are both —H;

$R_1$ and $R_2$ are both cyclopropyl; $R_3$ and $R_4$ are both ethyl; $R_5$ and $R_6$ are both —H;

$R_1$ and $R_2$ are both cyclopropyl; $R_3$ and $R_4$ are both methyl; $R_5$ is methyl; $R_6$ is —H;

$R_1$ and $R_2$ are both 1-methylcyclopropyl; $R_3$ and $R_4$ are both methyl; $R_5$ and $R_6$ are both —H;

$R_1$ and $R_2$ are both 1-methylcyclopropyl; $R_3$ and $R_4$ are both methyl; $R_5$ is methyl and $R_6$ is —H;

$R_1$ and $R_2$ are both 1-methylcyclopropyl; $R_3$ and $R_4$ are both methyl; $R_5$ is ethyl and $R_6$ is —H;

$R_1$ and $R_2$ are both 1-methylcyclopropyl; $R_3$ and $R_4$ are both methyl; $R_5$ is n-propyl and $R_6$ is —H;

$R_1$ and $R_2$ are both 1-methylcyclopropyl; $R_3$ and $R_4$ are both methyl; $R_5$ and $R_6$ are both methyl;

$R_1$ and $R_2$ are both 1-methylcyclopropyl; $R_3$ and $R_4$ are both ethyl; $R_5$ and $R_6$ are both —H;

$R_1$ and $R_2$ are both 1-methylcyclopropyl; $R_3$ is methyl, and $R_4$ is ethyl; $R_5$ and $R_6$ are both —H;

$R_1$ and $R_2$ are both 2-methylcyclopropyl; $R_3$ and $R_4$ are both methyl; $R_5$ and $R_6$ are both —H;

$R_1$ and $R_2$ are both 2-phenylcyclopropyl; $R_3$ and $R_4$ are both methyl; $R_5$ and $R_6$ are both —H;

$R_1$ and $R_2$ are both 1-phenylcyclopropyl; $R_3$ and $R_4$ are both methyl; $R_5$ and $R_6$ are both —H;

$R_1$ and $R_2$ are both cyclobutyl; $R_3$ and $R_4$ are both methyl; $R_5$ and $R_6$ are both —H;

$R_1$ and $R_2$ are both cyclopentyl; $R_3$ and $R_4$ are both methyl; $R_5$ and $R_6$ are both —H;

$R_1$ and $R_2$ are both cyclohexyl; $R_3$ and $R_4$ are both methyl; $R_5$ and $R_6$ are both —H;

$R_1$ and $R_2$ are both cyclohexyl; $R_3$ and $R_4$ are both phenyl; $R_5$ and $R_6$ are both —H;

$R_1$ and $R_2$ are both methyl; $R_3$ and $R_4$ are both methyl; $R_5$ and $R_6$ are both —H;

$R_1$ and $R_2$ are both methyl; $R_3$ and $R_4$ are both t-butyl; $R_5$ and $R_6$ are both —H;

$R_1$ and $R_2$ are both methyl; $R_3$ and $R_4$ are both phenyl; $R_5$ and $R_6$ are both —H;

$R_1$ and $R_2$ are both t-butyl; $R_3$ and $R_4$ are both methyl; $R_5$ and $R_6$ are both —H;

$R_1$ and $R_2$ are both ethyl; $R_3$ and $R_4$ are both methyl; $R_5$ and $R_6$ are both —H; or $R_1$ and $R_2$ are both n-propyl; $R_3$ and $R_4$ are both methyl; $R_5$ and $R_6$ are both —H.

12. The compound of claim 11, wherein the compound is represented by the following structural formula:

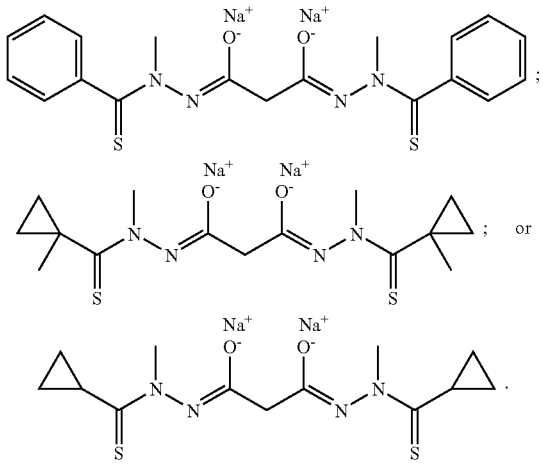

13. A pharmaceutical composition comprising a pharmaceutically acceptable carrier or diluent and a compound represented by the following structural formula:

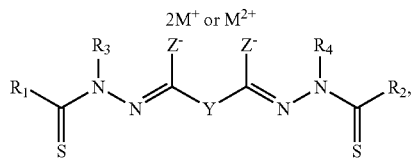

wherein:
Y is a covalent bond or a substituted or unsubstituted straight chained hydrocarbyl group;

$R_1$-$R_4$ are independently —H, an aliphatic group, a substituted aliphatic group, an aryl group or a substituted aryl group, or $R_1$ and $R_3$ taken together with the carbon and nitrogen atoms to which they are bonded, and/or $R_2$ and $R_4$ taken together with the carbon and nitrogen atoms to which they are bonded, form a non-aromatic heterocyclic ring optionally fused to an aromatic ring;

Z is —O or —S; and $M^+$ is a pharmaceutically acceptable monovalent cation and $M^{2+}$ is a pharmaceutically acceptable divalent cation.

14. The pharmaceutical composition of claim 13, wherein the compound is represented by the following structural formula:

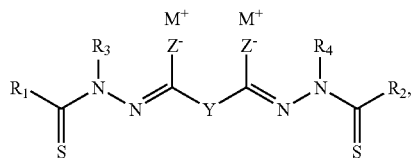

wherein $M^+$ is $Na^+$ or $K^+$.

15. The pharmaceutical composition of claim 14, wherein Z is O; $R_1$ and $R_2$ are the same; and $R_3$ and $R_4$ are the same.

16. The pharmaceutical composition of claim 15, wherein:

Y is a covalent bond, —C(R$_5$R$_6$)—, —(CH$_2$CH$_2$)—, trans-(CH=CH)—, cis-(CH=CH)— or —(CC)— group; and R$_5$ and R$_6$ are each independently —H, an aliphatic or substituted aliphatic group, or R$_5$ is —H and R$_6$ is a substituted or unsubstituted aryl group, or, R$_5$ and R$_6$, taken together, are a C2-C6 substituted or unsubstituted alkylene group.

17. The pharmaceutical composition of claim 16, wherein:
Y is —C(R$_5$R$_6$)—;
R$_1$ and R$_2$ are each a substituted or unsubstituted aryl group; and
R$_3$ and R$_4$ are each a substituted or unsubstituted aliphatic group.

18. The pharmaceutical composition of claim 17, wherein R$_5$ is —H and R$_6$ is —H, an aliphatic or substituted aliphatic group; R$_3$ and R$_4$ are each an alkyl group; and R$_6$ is —H or methyl.

19. The pharmaceutical composition of claim 18, wherein R$_1$ and R$_2$ are each a substituted or unsubstituted phenyl group and R$_3$ and R$_4$ are each methyl or ethyl.

20. The pharmaceutical composition of claim 19, wherein Y is —CR$_5$R$_6$—;
R$_1$ R$_2$ are both a substituted or unsubstituted aliphatic group;
R$_5$ is —H; and
R$_6$ is —H or an optionally substituted aliphatic group.

21. The pharmaceutical composition of claim 20, wherein R$_1$ and R$_2$ are both a C3-C8 cycloalkyl group optionally substituted with at least one alkyl group; R$_3$ and R$_4$ are both a substituted an alkyl group; and R$_6$ is —H or methyl.

22. The pharmaceutical composition of claim 13, wherein the compound is represented by the following structural formula:

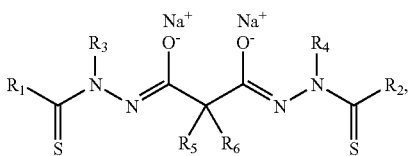

wherein:
R$_1$ and R$_2$ are both phenyl; R$_3$ and R$_4$ are both methyl; R$_5$ and R$_6$ are both —H;

R$_1$ and R$_2$ are both phenyl; R$_3$ and R$_4$ are both ethyl; R$_5$ and R$_6$ are both —H;

R$_1$ and R$_2$ are both 4-cyanophenyl; R$_3$ and R$_4$ are both methyl; R$_5$ is methyl; R$_6$ is —H;

R$_1$ and R$_2$ are both 4-methoxyphenyl; R$_3$ and R$_4$ are both methyl; R$_5$ and R$_6$ are both —H;

R$_1$ and R$_2$ are both phenyl; R$_3$ and R$_4$ are both methyl; R$_5$ is methyl; R$_6$ is —H;

R$_1$ and R$_2$ are both phenyl; R$_3$ and R$_4$ are both ethyl; R$_5$ is methyl; R$_6$ is —H;

R$_1$ and R$_2$ are both 4-cyanophenyl; R$_3$ and R$_4$ are both methyl; R$_5$ and R$_6$ are both —H;

R$_1$ and R$_2$ are both 2,5-dimethoxyphenyl; R$_3$ and R$_4$ are both methyl; R$_5$ and R$_6$ are both —H;

R$_1$ and R$_2$ are both 2,5-dimethoxyphenyl; R$_3$ and R$_4$ are both methyl; R$_5$ is methyl; R$_6$ is —H;

R$_1$ and R$_2$ are both 3-cyanophenyl; R$_3$ and R$_4$ are both methyl; R$_5$ and R$_6$ are both —H;

R$_1$ and R$_2$ are both 3-fluorophenyl; R$_3$ and R$_4$ are both methyl; R$_5$ and R$_6$ are both —H;

R$_1$ and R$_2$ are both 4-chlorophenyl; R$_3$ and R$_4$ are both methyl; R$_5$ is methyl; R$_6$ is —H;

R$_1$ and R$_2$ are both 2-dimethoxyphenyl; R$_3$ and R$_4$ are both methyl; R$_5$ and R$_6$ are both —H;

R$_1$ and R$_2$ are both 3-methoxyphenyl; R$_3$ and R$_4$ are both methyl; R$_5$ and R$_6$ are both —H;

R$_1$ and R$_2$ are both 2,3-dimethoxyphenyl; R$_3$ and R$_4$ are both methyl; R$_5$ and R$_6$ are both —H;

R$_1$ and R$_2$ are both 2,3-dimethoxyphenyl; R$_3$ and R$_4$ are both methyl; R$_5$ is methyl; R$_6$ is —H;

R$_1$ and R$_2$ are both 2,5-difluorophenyl; R$_3$ and R$_4$ are both methyl; R$_5$ and R$_6$ are both —H;

R$_1$ and R$_2$ are both 2,5-difluorophenyl; R$_3$ and R$_4$ are both methyl; R$_5$ is methyl; R$_6$ is —H;

R$_1$ and R$_2$ are both 2,5-dichlorophenyl; R$_3$ and R$_4$ are both methyl; R$_5$ and R$_6$ are both —H;

R$_1$ and R$_2$ are both 2,5-dimethylphenyl; R$_3$ and R$_4$ are both methyl; R$_5$ and R$_6$ are both —H;

R$_1$ and R$_2$ are both 2,5-dimethoxyphenyl; R$_3$ and R$_4$ are both methyl; R$_5$ and R$_6$ are both —H;

R$_1$ and R$_2$ are both phenyl; R$_3$ and R$_4$ are both methyl; R$_5$ and R$_6$ are both —H;

R$_1$ and R$_2$ are both 2,5-dimethoxyphenyl; R$_3$ and R$_4$ are both methyl; R$_5$ is methyl; R$_6$ is —H;

R$_1$ and R$_2$ are both cyclopropyl; R$_3$ and R$_4$ are both methyl; R$_5$ and R$_6$ are both —H;

R$_1$ and R$_2$ are both cyclopropyl; R$_3$ and R$_4$ are both ethyl; R$_5$ and R$_6$ are both —H;

R$_1$ and R$_2$ are both cyclopropyl; R$_3$ and R$_4$ are both methyl; R$_5$ is methyl; R$_6$ is —H;

R$_1$ and R$_2$ are both 1-methylcyclopropyl; R$_3$ and R$_4$ are both methyl; R$_5$ and R$_6$ are both —H;

R$_1$ and R$_2$ are both 1-methylcyclopropyl; R$_3$ and R$_4$ are both methyl; R$_5$ is methyl and R$_6$ is —H;

R$_1$ and R$_2$ are both 1-methylcyclopropyl; R$_3$ and R$_4$ are both methyl; R$_5$ is ethyl and R$_6$ is —H;

R$_1$ and R$_2$ are both 1-methylcyclopropyl; R$_3$ and R$_4$ are both methyl; R$_5$ is n-propyl and R$_6$ is —H;

R$_1$ and R$_2$ are both 1-methylcyclopropyl; R$_3$ and R$_4$ are both methyl; R$_5$ and R$_6$ are both methyl;

R$_1$ and R$_2$ are both 1-methylcyclopropyl; R$_3$ and R$_4$ are both ethyl; R$_5$ and R$_6$ are both —H;

R$_1$ and R$_2$ are both 1-methylcyclopropyl; R$_3$ is methyl, and R$_4$ is ethyl; R$_5$ and R$_6$ are both —H;

R$_1$ and R$_2$ are both 2-methylcyclopropyl; R$_3$ and R$_4$ are both methyl; R$_5$ and R$_6$ are both —H;

R$_1$ and R$_2$ are both 2-phenylcyclopropyl; R$_3$ and R$_4$ are both methyl; R$_5$ and R$_6$ are both —H;

R$_1$ and R$_2$ are both 1-phenylcyclopropyl; R$_3$ and R$_4$ are both methyl; R$_5$ and R$_6$ are both —H;

R$_1$ and R$_2$ are both cyclobutyl; R$_3$ and R$_4$ are both methyl; R$_5$ and R$_6$ are both —H;

R$_1$ and R$_2$ are both cyclopentyl; R$_3$ and R$_4$ are both methyl; R$_5$ and R$_6$ are both —H;

R$_1$ and R$_2$ are both cyclohexyl; R$_3$ and R$_4$ are both methyl; R$_5$ and R$_6$ are both —H;

R$_1$ and R$_2$ are both cyclohexyl; R$_3$ and R$_4$ are both phenyl; R$_5$ and R$_6$ are both —H;

R$_1$ and R$_2$ are both methyl; R$_3$ and R$_4$ are both methyl; R$_5$ and R$_6$ are both —H;

R$_1$ and R$_2$ are both methyl; R$_3$ and R$_4$ are both t-butyl; R$_5$ and R$_6$ are both —H;

R$_1$ and R$_2$ are both methyl; R$_3$ and R$_4$ are both phenyl; R$_5$ and R$_6$ are both —H;

R$_1$ and R$_2$ are both t-butyl; R$_3$ and R$_4$ are both methyl; R$_5$ and R$_6$ are both —H;

$R_1$ and $R_2$ are ethyl; $R_3$ and $R_4$ are both methyl; $R_5$ and $R_6$ are both —H; or $R_1$ and $R_2$ are both n-propyl; $R_3$ and $R_4$ are both methyl; $R_5$ and $R_6$ are both —H.

23. The pharmaceutical composition of claim 22, wherein the compound is represented by the following structural formula:

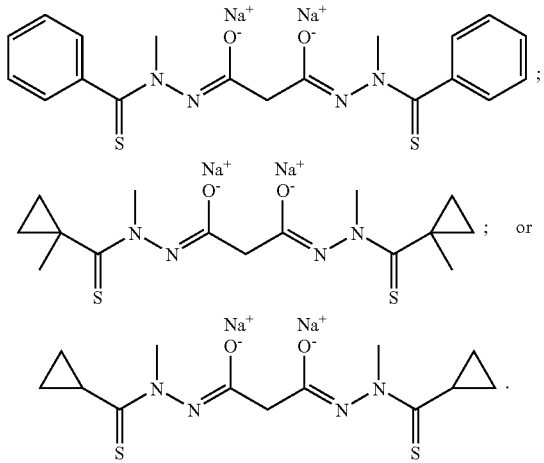

24. A method of treating a subject with melanoma, said method comprising administering to the subject an effective amount of a compound represented by the following structural formula:

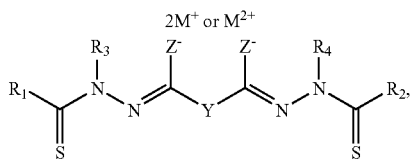

wherein:
Y is a covalent bond or a substituted or unsubstituted straight chained hydrocarbyl group;
$R_1$-$R_4$ are independently —H, an aliphatic group, a substituted aliphatic group, an aryl group or a substituted aryl group, or $R_1$ and $R_3$ taken together with the carbon and nitrogen atoms to which they are bonded, and/or $R_2$ and $R_4$ taken together with the carbon and nitrogen atoms to which they are bonded, form a non-aromatic heterocyclic ring optionally fused to an aromatic ring;
Z is —O or —S; and
$M^+$ is a pharmaceutically acceptable monovalent cation and $M^{2+}$ is a pharmaceutically acceptable divalent cation.

25. The method of claim 24, wherein the melanoma is multi-drug resistant.

26. The method of claim 24, wherein the compound is co-administered with an anti-cancer agent that stabilizes microtubules.

27. The method of claim 24, wherein the compound is co-administered with paclitaxel or an analog of paclitaxel.

28. The method of claim 24, wherein:
Z is O;
$R_1$ and $R_2$ are the same;
$R_3$ and $R_4$ are the same;
Y is a covalent bond, —C($R_5R_6$)—, —($CH_2CH_2$)—, trans-(CH=CH)—, cis-(CH=CH)— or —(CC)— group; and
$R_5$ and $R_6$ are each independently —H, an aliphatic or substituted aliphatic group, or $R_5$ is —H and $R_6$ is a substituted or unsubstituted aryl group, or $R_5$ and $R_6$, taken together, are a C2-C6 substituted or unsubstituted alkylene group.

29. The method of claim 28, wherein the compound represented by the following structural formula:

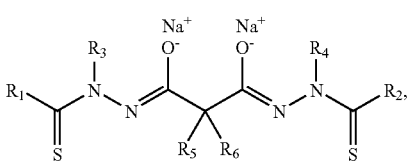

wherein:
$R_1$ and $R_2$ are both phenyl; $R_3$ and $R_4$ are both methyl; $R_5$ and $R_6$ are both —H;
$R_1$ and $R_2$ are both phenyl; $R_3$ and $R_4$ are both ethyl; $R_5$ and $R_6$ are both —H;
$R_1$ and $R_2$ are both 4-cyanophenyl; $R_3$ and $R_4$ are both methyl; $R_5$ is methyl; $R_6$ is —H;
$R_1$ and $R_2$ are both 4-methoxyphenyl; $R_3$ and $R_4$ are both methyl; $R_5$ and $R_6$ are both —H;
$R_1$ and $R_2$ are both phenyl; $R_3$ and $R_4$ are both methyl; $R_5$ is methyl; $R_6$ is —H;
$R_1$ and $R_2$ are both phenyl; $R_3$ and $R_4$ are both ethyl; $R_5$ is methyl; $R_6$ is —H;
$R_1$ and $R_2$ are both 4-cyanophenyl; $R_3$ and $R_4$ are both methyl; $R_5$ and $R_6$ are both —H;
$R_1$ and $R_2$ are both 2,5-dimethoxyphenyl; $R_3$ and $R_4$ are both methyl; $R_5$ and $R_6$ are both —H;
$R_1$ and $R_2$ are both 2,5-dimethoxyphenyl; $R_3$ and $R_4$ are both methyl; $R_5$ is methyl; $R_6$ is —H;
$R_1$ and $R_2$ are both 3-cyanophenyl; $R_3$ and $R_4$ are both methyl; $R_5$ and $R_6$ are both —H;
$R_1$ and $R_2$ are both 3-fluorophenyl; $R_3$ and $R_4$ are both methyl; $R_5$ and $R_6$ are both —H;
$R_1$ and $R_2$ are both 4-chlorophenyl; $R_3$ and $R_4$ are both methyl; $R_5$ is methyl; $R_6$ is —H;
$R_1$ and $R_2$ are both 2-dimethoxyphenyl; $R_3$ and $R_4$ are both methyl; $R_5$ and $R_6$ are both —H;
$R_1$ and $R_2$ are both 3-methoxyphenyl; $R_3$ and $R_4$ are both methyl; $R_5$ and $R_6$ are both —H;
$R_1$ and $R_2$ are both 2,3-dimethoxyphenyl; $R_3$ and $R_4$ are both methyl; $R_5$ and $R_6$ are both —H;
$R_1$ and $R_2$ are both 2,3-dimethoxyphenyl; $R_3$ and $R_4$ are both methyl; $R_5$ is methyl; $R_6$ is —H;
$R_1$ and $R_2$ are both 2,5-difluorophenyl; $R_3$ and $R_4$ are both methyl; $R_5$ and $R_6$ are both —H;
$R_1$ and $R_2$ are both 2,5-difluorophenyl; $R_3$ and $R_4$ are both methyl; $R_5$ is methyl; $R_6$ is —H;
$R_1$ and $R_2$ are both 2,5-dichlorophenyl; $R_3$ and $R_4$ are both methyl; $R_5$ and $R_6$ are both —H;
$R_1$ and $R_2$ are both 2,5-dimethylphenyl; $R_3$ and $R_4$ are both methyl; $R_5$ and $R_6$ are both —H;
$R_1$ and $R_2$ are both 2,5-dimethoxyphenyl; $R_3$ and $R_4$ are both methyl; $R_5$ and $R_6$ are both —H;
$R_1$ and $R_2$ are both phenyl; $R_3$ and $R_4$ are both methyl; $R_5$ and $R_6$ are both —H;
$R_1$ and $R_2$ are both 2,5-dimethoxyphenyl; $R_3$ and $R_4$ are both methyl; $R_5$ is methyl; $R_6$ is —H;

R₁ and R₂ are both cyclopropyl; R₃ and R₄ are both methyl; R₅ and R₆ are both —H;
R₁ and R₂ are both cyclopropyl; R₃ and R₄ are both ethyl; R₅ and R₆ are both —H;
R₁ and R₂ are both cyclopropyl; R₃ and R₄ are both methyl; R₅ is methyl; R₆ is —H;
R₁ and R₂ are both 1-methylcyclopropyl; R₃ and R₄ are both methyl; R₅ and R₆ are both —H;
R₁ and R₂ are both 1-methylcyclopropyl; R₃ and R₄ are both methyl; R₅ is methyl and R₆ is —H;
R₁ and R₂ are both 1-methylcyclopropyl; R₃ and R₄ are both methyl; R₅ is ethyl and R₆ is —H;
R₁ and R₂ are both 1-methylcyclopropyl; R₃ and R₄ are both methyl; R₅ is n-propyl and R₆ is —H;
R₁ and R₂ are both 1-methylcyclopropyl; R₃ and R₄ are both methyl; R₅ and R₆ are both methyl;
R₁ and R₂ are both 1-methylcyclopropyl; R₃ and R₄ are both ethyl; R₅ and R₆ are both —H;
R₁ and R₂ are both 1-methylcyclopropyl; R₃ is methyl, and R₄ is ethyl; R₅ and R₆ are both —H;
R₁ and R₂ are both 2-methylcyclopropyl; R₃ and R₄ are both methyl; R₅ and R₆ are both —H;
R₁ and R₂ are both 2-phenylcyclopropyl; R₃ and R₄ are both methyl; R₅ and R₆ are both —H;
R₁ and R₂ are both 1-phenylcyclopropyl; R₃ and R₄ are both methyl; R₅ and R₆ are both —H;
R₁ and R₂ are both cyclobutyl; R₃ and R₄ are both methyl; R₅ and R₆ are both —H;
R₁ and R₂ are both cyclopentyl; R₃ and R₄ are both methyl; R₅ and R₆ are both —H;
R₁ and R₂ are both cyclohexyl; R₃ and R₄ are both methyl; R₅ and R₆ are both —H;
R₁ and R₂ are both cyclohexyl; R₃ and R₄ are both phenyl; R₅ and R₆ are both —H;
R₁ and R₂ are both methyl; R₃ and R₄ are both methyl; R₅ and R₆ are both —H;
R₁ and R₂ are both methyl; R₃ and R₄ are both t-butyl; R₅ and R₆ are both —H;
R₁ and R₂ are both methyl; R₃ and R₄ are both phenyl; R₅ and R₆ are both —H;
R₁ and R₂ are both t-butyl; R₃ and R₄ are both methyl; R₅ and R₆ are both —H;
R₁ and R₂ are ethyl; R₃ and R₄ are both methyl; R₅ and R₆ are both —H; or
R₁ and R₂ are both n-propyl; R₃ and R₄ are both methyl; R₅ and R₆ are both —H.

30. A method of preparing a bis(thio-hydrazide amide) disalt, comprising the steps of:
combining a neutral bis(thio-hydrazide amide), an organic solvent and a base to form a bis(thio-hydrazide amide) solution; and
combining the solution and an organic antisolvent, thereby precipitating a disalt of the bis(thio-hydrazide amide) from the bis(thio-hydrazide amide) solution.

31. The method of claim 30, wherein the neutral bis(thio-hydrazide amide) is represented by the following Structural Formula:

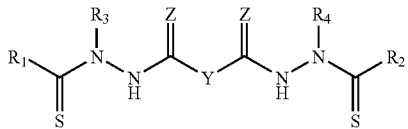

wherein:
Y is a covalent bond or an optionally substituted straight chained hydrocarbyl group;
R₁-R₄ are independently —H, an optionally substituted aliphatic group, an optionally substituted aryl group, or R₁ and R₃ taken together with the carbon and nitrogen atoms to which they are bonded, and/or R₂ and R₄ taken together with the carbon and nitrogen atoms to which they are bonded, form a non-aromatic heterocyclic ring optionally fused to an aromatic ring; and
Z is O or S.

32. The method of claim 24, wherein the subject is a human.

33. A method of treating a subject with melanoma, said method comprising administering to the subject an effective amount of a compound represented by the following structural formula:

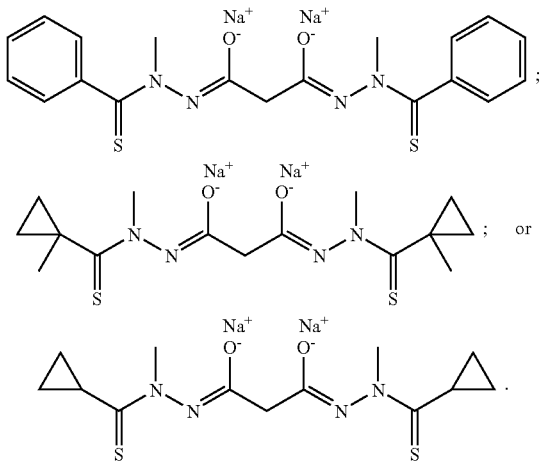

in combination with paclitaxel or an analog of paclitaxel.

34. The method of claim 33, wherein the subject is a human.

* * * * *

UNITED STATES PATENT AND TRADEMARK OFFICE
CERTIFICATE OF CORRECTION

PATENT NO. : 7,385,084 B2
APPLICATION NO. : 11/157213
DATED : June 10, 2008
INVENTOR(S) : Keizo Koya et al.

It is certified that error appears in the above-identified patent and that said Letters Patent is hereby corrected as shown below:

Column 31, Claim 2, line 61, delete "$K^{30}$" and insert -- $K^+$ --

Column 36, Claim 22, line 15, delete "2,5-dichiorophenyl" and insert -- 2,5-dichlorophenyl --

Signed and Sealed this

Eleventh Day of November, 2008

JON W. DUDAS
*Director of the United States Patent and Trademark Office*